United States Patent
Bonda et al.

(10) Patent No.: US 7,588,702 B2
(45) Date of Patent: *Sep. 15, 2009

(54) METHOD OF QUENCHING ELECTRONIC EXCITATION OF CHROMOPHORE-CONTAINING ORGANIC MOLECULES IN PHOTOACTIVE COMPOSITIONS

(75) Inventors: Craig A. Bonda, Winfield, IL (US); Anna Pavlovic, Elmwood Park, IL (US)

(73) Assignee: Hallstar Innovations Corp., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/022,758

(22) Filed: Jan. 30, 2008

(65) Prior Publication Data

US 2009/0041847 A1   Feb. 12, 2009

Related U.S. Application Data

(63) Continuation-in-part of application No. 11/891,281, filed on Aug. 9, 2007.

(51) Int. Cl.
  F21V 9/04 (2006.01)
  F21V 9/06 (2006.01)
  G02B 5/22 (2006.01)
  G02B 5/26 (2006.01)

(52) U.S. Cl. ............... 252/589; 424/59; 424/60; 424/401; 514/520; 524/90; 558/410

(58) Field of Classification Search ............... 252/589; 424/59, 60, 401; 514/520; 524/90; 558/410
  See application file for complete search history.

(56) References Cited

U.S. PATENT DOCUMENTS

| | | |
|---|---|---|
| 2,623,060 A | 12/1952 | Cragoe |
| 3,215,724 A | 11/1965 | Strobel et al. |
| 3,337,357 A | 8/1967 | Strobel et al. |

(Continued)

FOREIGN PATENT DOCUMENTS

| | | |
|---|---|---|
| DE | 1222926 | 8/1966 |

(Continued)

OTHER PUBLICATIONS

Katritzky, Alan R.; Nair, Satheesh K.; Witek, Rachel M.; Hutchins, Steven M. Synthesis of 3,3-diarylpyrrolidines from diaryl ketones, ARKIVOC (Gainesville, FL, United States) (2003), (5),pp. 9-18 Arkat USA Inc. URL: http://www.arkatusa.org/zark/journal/2003/Bernath/GB-594J/594J.pdf.*

(Continued)

Primary Examiner—Ling-Siu Choi
Assistant Examiner—Bijan Ahvazi
(74) Attorney, Agent, or Firm—Marshall, Gerstein & Borun LLP

(57) ABSTRACT

The photostabilizing electronic excited state energy—particularly singlet state energy from a UV-absorbing molecule has been found to be readily transferred to (accepted by) α-cyanodiphenylacrylate compounds of formulas (I) and (V) having an alkoxy radical preferably in the four (para) position (hereinafter methoxycrylenes) on one or both of the phenyl rings:

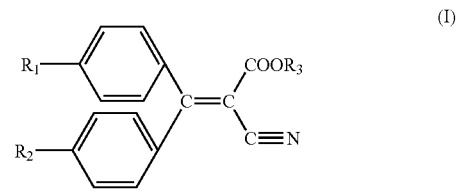

(I)

wherein at least one of $R_1$ and $R_2$ is a straight or branched chain $C_1$-$C_{12}$ alkoxy radical, preferably $C_1$-$C_8$, more preferably $C_1$-$C_4$, and most preferably methoxy, and any non-alkoxy radical $R_1$ or $R_2$ is hydrogen; and $R_3$ is a straight or branched chain $C_1$-$C_{24}$ alkyl radical, preferably $C_{12}$-$C_{24}$, more preferably $C_{20}$;

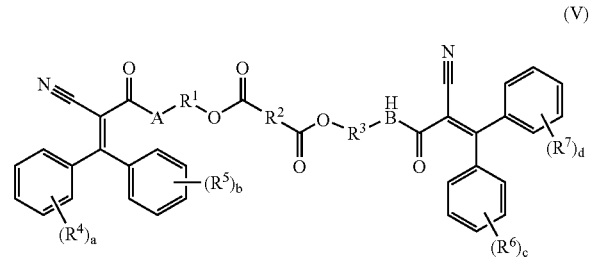

(V)

wherein A and B are the same or different and are selected from the group consisting of oxygen, amino and sulfur; $R^1$ and $R^3$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^2$ is selected from the group consisting of $C_1$-$C_{30}$ alkyl, $C_2$-$C_{30}$ alkylene, $C_2C_{30}$ alkyne, $C_3$-$C_8$ cycloalkyl, $C_1$-$C_{30}$ substituted alkyl, $C_3$-$C_8$ substituted cycloalkyl, $C_1$-$C_{30}$ substituted alkylene, $C_2$-$C_{30}$ substituted alkyne; $R^4$, $R^5$, $R^6$ and $R^7$ are the same or different and are selected from the group consisting of $C_1$-$C_{30}$ alkoxy straight chain or branched and a, b, c and d are each either 0 or 1, and a, b, c and d add up to 1, 2, 3, or 4.

12 Claims, 5 Drawing Sheets

U.S. PATENT DOCUMENTS

| | | | |
|---|---|---|---|
| 4,284,621 A | 8/1981 | Preuss et al. | |
| 4,307,240 A | 12/1981 | Ching | |
| 4,562,278 A | 12/1985 | Hill | |
| 5,576,354 A | 11/1996 | Deflandre et al. | |
| 5,738,842 A * | 4/1998 | Raspanti et al. | 424/59 |
| 5,783,307 A * | 7/1998 | Fagerburg et al. | 428/412 |
| 5,989,528 A | 11/1999 | Tanner et al. | |
| 6,113,931 A | 9/2000 | Bonda et al. | |
| 6,284,916 B1 | 9/2001 | Bonda et al. | |
| 6,485,713 B1 | 11/2002 | Bonda et al. | |
| 6,518,451 B2 | 2/2003 | Bonda et al. | |
| 6,537,529 B1 | 3/2003 | Bonda | |
| 6,551,605 B2 | 4/2003 | Bonda | |
| 6,800,274 B2 | 10/2004 | Bonda et al. | |
| 6,919,473 B2 | 7/2005 | Bonda et al. | |
| 6,962,692 B2 | 11/2005 | Bonda et al. | |
| 7,235,587 B2 | 6/2007 | Bonda et al. | |
| 2003/0000130 A1* | 1/2003 | Wood et al. | 44/275 |
| 2003/0176542 A1* | 9/2003 | Abe et al. | 524/91 |
| 2004/0047817 A1* | 3/2004 | Bonda | 424/59 |
| 2004/0047818 A1 | 3/2004 | Bonda | |
| 2004/0247539 A1 | 12/2004 | Wendel et al. | |
| 2005/0191249 A1 | 9/2005 | Bonda et al. | |
| 2006/0002869 A1 | 1/2006 | Bonda et al. | |

FOREIGN PATENT DOCUMENTS

| | | |
|---|---|---|
| EP | 1323743 | 7/2003 |
| JP | 2005139263 | 6/2005 |
| SU | 1273360 | 11/1986 |
| WO | WO-0027337 | 5/2000 |
| WO | WO-0242368 | 5/2002 |

OTHER PUBLICATIONS

Eric Chatelain and Bernard Gabard, Photostabilization of Butyl methoxydibenzoylmethane (Avobenzone) and Ethylhexyl methoxycinnamate by Bis-ethylhexyloxyphenol methoxyphenyl triazine (Tinosorb S), a New UV Broadband Filter, Photochemistry and Photobiology, 2001, 74(3): 401-406.*

Craig Bonda, Research Pathways to Photostable Sunscreens, Feb. 5, 2008, vol. 123, No. 2. pp. 1, 49-60. issue of Cosmetics & Toiletries Magazine.*

International Search Report for PCT/US2008/058456 dated Jun. 27, 2008.

Written Opinion for PCT/US2008/058456 dated Jun. 27, 2008.

N. G. Senchenya, et al., *Silicon-containing esters of α-cyanoacrylic acid: synthesis and properties*, Russian Chemical Bulletin, vol. 42, No. 5, May, 1993, pp. 909-911.

European Search Report for EP 08 10 3204, dated Jul. 17, 2008.

European Search Report for EP 08 10 3205, dated Jul. 25, 2008.

* cited by examiner

METHOD OF QUENCHING ELECTRONIC EXCITATION OF CHROMOPHORE-CONTAINING ORGANIC MOLECULES IN PHOTOACTIVE COMPOSITIONS

CROSS-REFERENCE TO RELATED APPLICATION

This application is a continuation-in-part of application Ser. No. 11/891,281 filed Aug. 9, 2007. The entire text of the priority application is incorporated herein by reference in its entirety.

FIELD OF THE INVENTION

The present invention is directed to a method of quenching electronic excited state(s) of chromophore-containing UV-absorbing organic molecules in photoactive compositions. More particularly, it has been found that α-cyano-β,β diphenylacrylates (crylenes) having an alkoxy radical, preferably on one of the phenyl rings (alternatively on both phenyl rings), quenches the excited state of the chromophore by accepting the excited state energy (singlet and sometimes also the triplet state), thereby returning the UV-absorbing molecule back to its ground state so that the chromophore can absorb more photons, e.g., from ultraviolet (UV) light, thereby photostabilizing UV-absorbing chromophore-containing organic molecules, particularly butyl methoxydibenzoylmethane (Avobenzone), octyl methoxycinnamate (Octinoxate), and octyl salicylate (Octisalate) in photoactive compositions.

BACKGROUND

The absorption of ultraviolet light by a chromophore-containing organic molecule causes the excitation of an electron in the chromophore moiety from an initially occupied, low energy orbital to a higher energy, previously unoccupied orbital. The energy of the absorbed photon is used to energize an electron and cause it to "jump" to a higher energy orbital, see Turro, Modern Molecular Photochemistry, 1991. Two excited electronic states derive from the electronic orbital configuration produced by UV light absorption. In one state, the electron spins are paired (antiparallel) and in the other state the electron spins are unpaired (parallel). The state with paired spins has no resultant spin magnetic moment, but the state with unpaired spins possesses a net spin magnetic moment. A state with paired spins remains a single state in the presence of a magnetic field, and is termed a singlet state. A state with unpaired spins interacts with a magnetic field and splits into three quantized states, and is termed a triplet state.

In the electronically excited state, the chromophore-containing organic molecule is prone to degrade via a number of known pathways and, therefore, can absorb little or no additional UV light. To photostabilize an electronically excited chromophore-containing organic molecule in order to provide sufficient UV protection, it must be returned to the ground state before it undergoes a photochemical reaction destructive to its UV absorbing capability. There are known photostabilizing sunscreen additives, such as Octocrylene, methylbenzilydene camphor, and the esters or polyesters of naphthalene dicarboxylic acid of this assignee's U.S. Pat. Nos. 6,113,931; 6,284,916; 6,518,451; and 6,551,605, all hereby incorporated by reference, that are capable of quenching excited triplet state energy. Surprisingly, it has been found that alkoxy crylenes, particularly methoxy crylenes, return chromophore-containing organic molecules, particularly butyl methoxydibenzoylmethane (Avobenzone), octyl methoxycinnamate (Octinoxate), and octyl salicylate (Octisalate), from both an electronically excited singlet state and excited triplet state back to their ground state, thereby photostabilizing the UV-absorbing organic molecules.

Deflandre U.S. Pat. No. 5,576,354 generally discloses a cosmetic sunscreen composition containing at least 1% by weight of an α-cyano-β,β-diphenylacrylate that will photostabilize a dibenzoylmethane derivative, e.g., Parsol 1789 (Avobenzone), so long as the composition contains a fatty phase, e.g., glycerol stearates, isopropyl myristate or the like, and so long as the mole ratio of the α-cyano-β,β-diphenylacrylate to the dibenzoylmethane derivative is at least 0.8. The compounds preferred in the '354 patent and disclosed in the examples are octocrylene, which contains no alkoxy radical(s) (UVINULN 539); β,β-bis(4-methoxyphenyl)acrylates (containing no cyano radical); and the α-cyano-β,β-diphenylacrylates, which contain no alkoxy radical(s).

As stated in this assignees pending application Ser. Nos. 10/241,388; 10/361,223; and 10/786,793, an α-cyano-β,β-diphenylacrylate compound (e.g., octocrylene) is known to quench (accept) the excited triplet state energy of an excited photoactive compound by dissipating the energy kinetically in the form of rapid isomerizations. This process is shown below:

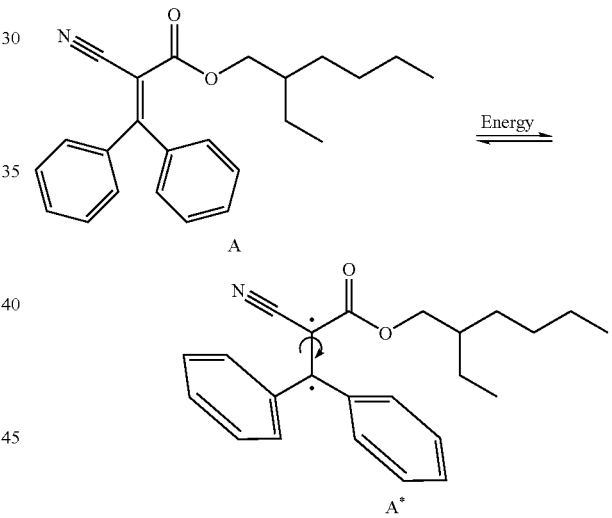

wherein the α-cyano-β,β-diphenylacrylate compound (octocrylene shown above as structure A), accepts the triplet excited state energy from a photoactive compound and forms a diradical (shown above as structure A*) at the α and β positions of the acrylate, which converts the double bond into a single bond and allows for the free rotation of the phenyl groups. This rotation occurs rapidly and efficiently to dissipate any excited triplet state energy accepted by the α-cyano-β,β-diphenylacrylate compound from the photoactive compound.

While octocrylene is able to quench (accept) the triplet excited state energy from a photoactive compound, thereby photostabilizing, to some degree, dibenzoylmethane derivatives, as shown in examples 1, 4, 6 and 8 of Deflandre et al. U.S. Pat. No. 5,576,354, hereby incorporated by reference, there exists a need in the photoactive composition art to find one or more compounds that quench (accept) the singlet excited state energy and preferably also the triplet excited state energy from photoactive compounds, which octocrylene does not.

Quite surprisingly, it has been found that the alkoxy substituted α-cyano-β,β-diphenylacrylates (alkoxy crylenes) will quench the electronically excited singlet state energy of UV-absorbing organic molecules, such as the dibenzoylmethane derivatives of U.S. Pat. No. 5,576,354, even at very low loadings compared to the quantity of UV-absorbing compounds.

SUMMARY

The photostabilizing electronic excited state energy—particularly singlet state energy from a UV-absorbing molecule—has been found to be readily transferred to (accepted by) α-cyanodiphenylacrylate compounds having an alkoxy radical in the four (para) position (hereinafter "alkoxycrylenes") on one or both of the phenyl rings having the formula (I):

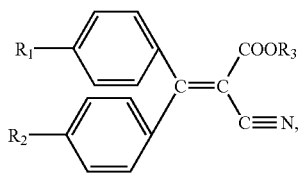

(I)

wherein one or both of $R_1$ and $R_2$ is a straight or branched chain $C_1$-$C_{30}$ alkoxy radical, preferably $C_1$-$C_8$, more preferably methoxy, and any non-alkoxy radical $R_1$ or $R_2$ is hydrogen; and $R_3$ is a straight or branched chain $C_1$-$C_{30}$ alkyl radical, preferably $C_2$-$C_{20}$.

DETAILED DESCRIPTION OF THE PREFERRED EMBODIMENTS

Figure 1:
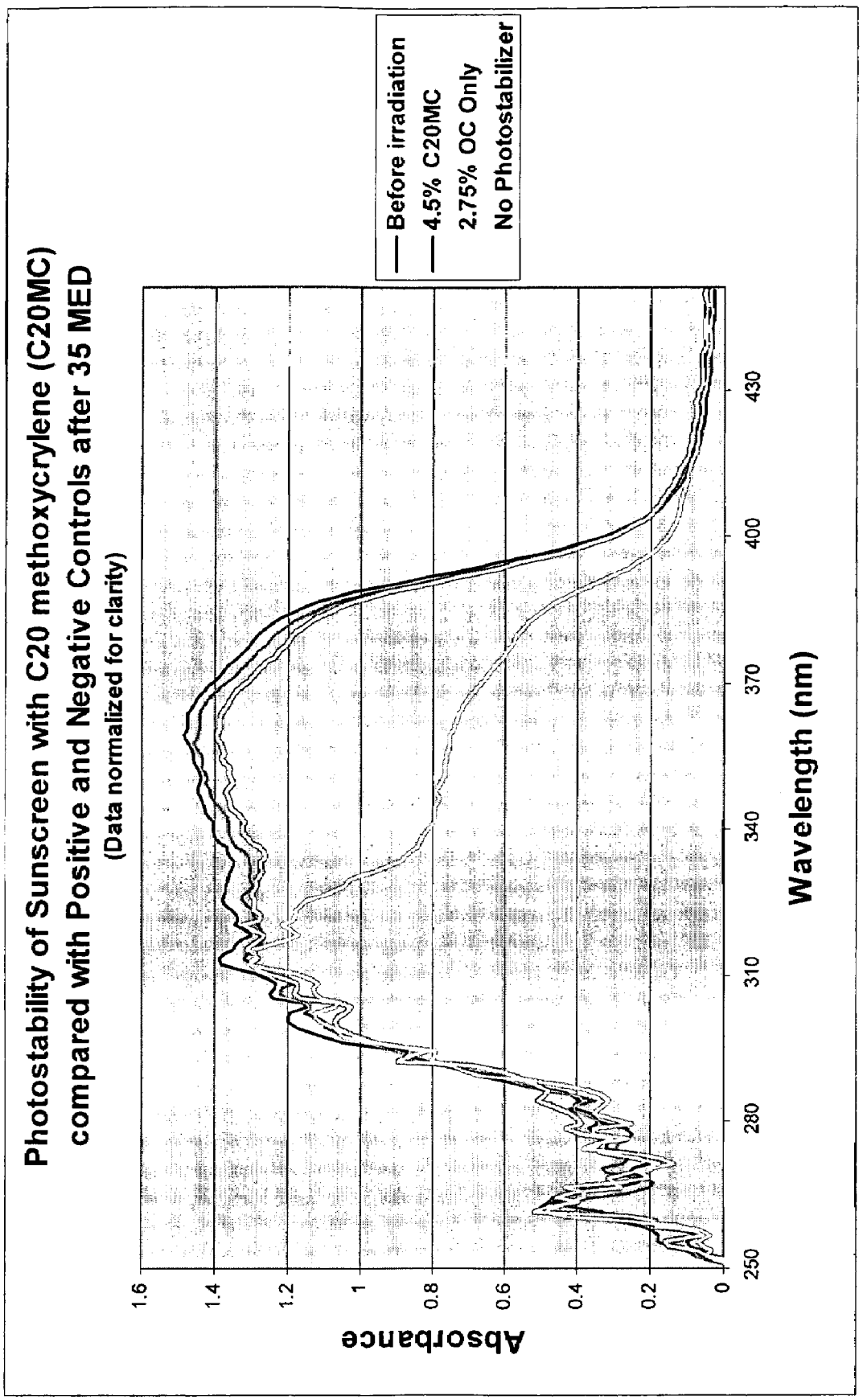
FIG. 1 is a graph showing the photostability of the sunscreen compositions of Examples 1-3 (when irradiated with 35 MED of UV radiation) provided by 4.5% octyldocedyl methoxy crylene (C2OMC); and 2.75% Octocrylene (OC) compared to the photostability prior to UV irradiation and compared to the composition with no photostabilizer.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The term "alkoxy" herein refers to a radical extending from the para position of one or both of the phenyl rings having the formula O—R, wherein R is an alkyl radical, straight chain or branched having 1 to 30 carbon atoms, preferably wherein R=$C_1$ to $C_8$, more preferably $C_2$-$C_{20}$, and most preferably —O—$CH_3$ (methoxy). The oxygen atom of the alkoxy radical is covalently bonded to the para carbon atom of one or both of the phenyl rings, preferably only one of the phenyls, preferably having the formula (II) or (III):

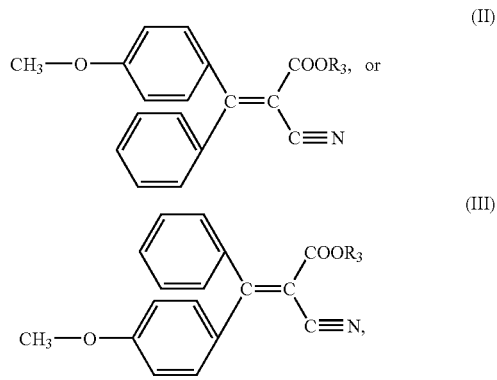

wherein $R_3$ is as previously defined.

The term "crylene" as used herein refers to a chromophoric moiety that includes an α-cyano-β,β-diphenyl propanoic acid ester.

The term "cyano" as used herein refers to a —C≡N group, also designated "—CN."

Photoactive compositions, e.g., sunscreen compositions, generally include UV-A and UV-B photoactive compounds in a cosmetically acceptable carrier, optionally including additives, such as emollients, stabilizers, emulsifiers, and combinations thereof. These additives can be used in preparing a UV filter composition in an emulsion (oil-in-water or water-in-oil) from a composition that includes one or more photoactive compounds and a solvent or a solvent combination that includes one or more organic solvents and water. When made, preferably the emulsion is an oil-in-water emulsion, wherein the oil phase is primarily formed from a mixture of the UV filter compound(s) and one or more organic solvents.

A typical photoactive composition includes one or more photoactive compounds, wherein the photoactive compound(s) act to absorb UV radiation and thereby protect the substrate (e.g., human skin, resins, films, and the like) from the harmful effects of UV radiation. The absorption process causes a photoactive compound to reach an excited state, wherein the excited state is characterized by the presence of excited electronic energy (e.g., singlet state energy or triplet state energy), as compared to the ground state of the photoactive compound. Once a photoactive compound reaches an excited state there exists a number of pathways by which the excited photoactive compound can dissipate its excess energy (e.g., singlet and/or triplet energy), however, many of those pathways adversely affect the ability of the photoactive compound to further absorb UV radiation. The alkoxy crylene molecules described herein accept electronic singlet excited state energy from UV-absorbers, particularly Avobenzone, octyl methoxycinnamate (Octinoxate), and octyl salicylate (Octisalate). The alkoxy crylenes also are very effective UVA absorbers in addition to providing electronic singlet state energy quenching of other UV-absorbing compounds in sunscreen compositions. The alkoxy crylene molecules described herein are especially effective when combined with one or more additional electronic singlet excited state quenching compounds such as oxybenzone. Particularly surprising photostabilization is achieved in sunscreen compositions containing the alkoxy crylene molecules described herein together with octyl methoxycinnamate and Avobenzone.

A photoactive compound is one that responds to light photoelectrically. In the compositions and methods of photostabilization disclosed herein, a photoactive compound is one that responds to UV radiation photoelectrically. For example, all photoactive compound-containing compositions that respond to UV radiation photoelectrically by photoactive compound photodegradation benefit highly by the inclusion of the alkoxy crylene molecules described herein. The alkoxy crylenes described herein are useful photostabilizers and/or photoactive compounds when combined with any single or combination photoactive compounds identified in Shaath, Nadim, Encyclopedia of UV filters, © 2007, hereby incorporated by reference. Photostability is a problem with all UV filters because they all reach an electronic singlet excited state upon exposure to UV radiation.

It is theorized that the following UV filters are photostabilized by the alkoxy crylene molecules described herein, including all of the following, including combinations of any two or more, and include compounds selected from the following categories (with specific examples) including: p-aminobenzoic acid, its salts and its derivatives (ethyl, isobutyl, glyceryl esters; p-dimethylaminobenzoic acid); anthranilates (o-aminobenzoates; methyl, menthyl, phenyl, benzyl, phenylethyl, linalyl, terpinyl, and cyclohexenyl esters); salicylates (octyl, amyl, phenyl, benzyl, menthyl (homosalate), glyceryl, and dipropyleneglycol esters); cinnamic acid derivatives (menthyl and benzyl esters, alpha-phenyl cinnamonitrile; butyl cinnamoyl pyruvate); dihydroxycinnamic acid derivatives (umbelliferone, methylumbelliferone, methylaceto-umbelliferone); camphor derivatives (3 benzylidene, 4 methylbenzylidene, polyacrylamidomethyl benzylidene, benzalkonium methosulfate, benzylidene camphor sulfonic acid, and terephthalylidene dicamphor sulfonic acid); trihydroxycinnamic acid derivatives (esculetin, methylesculetin, daphnetin, and the glucosides, esculin and daphnin); hydrocarbons (diphenylbutadiene, stilbene); dibenzalacetone; benzalacetophenone; naphtholsulfonates (sodium salts of 2-naphthol-3,6-disulfonic and of 2-naphthol-6,8-disulfonic acids); dihydroxy-naphthoic acid and its salts; o- and p-hydroxydiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric acid derivatives; vilouric acid derivatives; tannic acid and its derivatives; hydroquinone; and benzophenones (oxybenzone, sulisobenzone, dioxybenzone, benzoresorcinol, octabenzone, 4-isopropyldibenzoylmethane, butylmethoxydibenzoylmethane, etocrylene, and 4-isopropyl-dibenzoylmethane).

The following UV filters should be particularly photostabilized by the alkoxy crylene molecules described herein: 2-ethylhexyl p-methoxycinnamate, 4,4'-t-butyl methoxydibenzoylmethane, octyldimethyl p-aminobenzoate, digalloyltrioleate, ethyl 4-[bis(hydroxypropyl)]aminobenzoate, 2-ethylhexylsalicylate, glycerol p-aminobenzoate, 3,3,5-trimethylcyclohexylsalicylate, and combinations thereof.

Photoactive compositions disclosed herein can include a variety of photoactive compounds, preferably including one or more UV-A photoactive compounds and one or more UV-B photoactive compounds. Preferably, a sunscreen composition includes a photoactive compound selected from the group consisting of p-aminobenzoic acid and salts and derivatives thereof, anthranilate and derivatives thereof, dibenzoylmethane and derivatives thereof, salicylate and derivatives thereof, cinnamic acid and derivatives thereof, dihydroxycinnamic acid and derivatives thereof, camphor and salts and derivatives thereof, trihydroxycinnamic acid and derivatives thereof, dibenzalacetone naphtholsulfonate and salts and derivatives thereof, benzalacetophenone naphtholsulfonate and salts and derivatives thereof, dihydroxy-naphthoic acid and salts thereof, o-hydroxydiphenyldisulfonate and salts and derivatives thereof, p-hydroxydiphenyldisulfonate and salts and derivatives thereof, coumarin and derivatives thereof, diazole derivatives; quinine derivatives and salts thereof, quinoline derivatives; uric acid derivatives; vilouric acid derivatives; tannic acid and derivatives thereof, hydroquinone; diethylamino hydroxybenzoyl hexyl benzoate and salts and derivatives thereof, and combinations of the foregoing.

UV A radiation (about 320 nm to about 400 nm), is recognized as contributing to causing damage to skin, particularly to very lightly colored or sensitive skin. A sunscreen composition disclosed herein preferably includes a UV-A photoactive compound. Preferably, a sunscreen composition disclosed herein includes a dibenzoylmethane derivative UV-A photoactive compound. Preferred dibenzoylmethane derivatives include, 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof.

For a product marketed in the United States, preferred cosmetically acceptable photoactive compounds and concentrations (reported as a percentage by weight of the total cosmetic sunscreen composition) include: aminobenzoic acid (also called para aminobenzoic acid and PABA; 15% or less), Avobenzone (also called butyl methoxy dibenzoylmethane; 3% or less), cinoxate (also called 2 ethoxyethyl p methoxycinnamate; 3% or less), dioxybenzone (also called benzophenone 8; 3% or less), homosalate ((also called 3,3,5-trimethylcyclohexyl salicylate, 15% or less), menthyl anthranilate (also called menthyl 2 aminobenzoate; 5% or less), octocrylene (also called 2 ethylhexyl 2 cyano 3,3 diphenylacrylate; 10% or less), octyl methoxycinnamate (7.5% or less), octyl salicylate (also called 2 ethylhexyl salicylate; 5% or less), oxybenzone (also called benzophenone 3; 6% or less), padimate O (also called octyl dimethyl PABA; 8% or less), phenylbenzimidazole sulfonic acid (water soluble; 4% or less), sulisobenzone (also called benzophenone 4; 10% or less), titanium dioxide (25% or less), trolamine salicylate (also called triethanolamine salicylate; 12% or less), and zinc oxide (25% or less).

Other preferred cosmetically acceptable photoactive compounds and preferred concentrations (percent by weight of the total cosmetic sunscreen composition) include diethanolamine methoxycinnamate (10% or less), ethyl-[bis(hydroxypropyl)]aminobenzoate (5% or less), glyceryl aminobenzoate (3% or less), 4 isopropyl dibenzoylmethane (5% or less), 4 methylbenzylidene camphor (6% or less), terephthalylidene dicamphor sulfonic acid (10% or less), and sulisobenzone (also called benzophenone 4, 10% or less).

For a product marketed in the European Union, preferred cosmetically acceptable photoactive compounds and preferred concentrations (reported as a percentage by weight of the total cosmetic sunscreen composition) include: PABA (5% or less), camphor benzalkonium methosulfate (6% or less), homosalate (10% or less), benzophenone 3 (10% or less), phenylbenzimidazole sulfonic acid (8% or less, expressed as acid), terephthalidene dicamphor sulfonic acid (10% or less, expressed as acid), butyl methoxydibenzoylmethane (5% or less), benzylidene camphor sulfonic acid (6% or less, expressed as acid), octocrylene (10% or less, expressed as acid), polyacrylamidomethyl benzylidene camphor (6% or less), ethylhexyl methoxycinnamate (10% or less), PEG 25 PABA (10% or less), isoamyl p methoxycinnamate (10% or less), ethylhexyl triazone (5% or less), drometrizole trielloxane (15% or less), diethylhexyl butamido triazone (10% or less), 4 methylbenzylidene camphor (4% or less), 3 benzylidene camphor (2% or less), ethylhexyl salicylate (5% or less), ethylhexyl dimethyl PABA (8% or less), benzophenone 4 (5%, expressed as acid), methylene bis benztriazolyl tetramethylbutylphenol (10% or less), disodium phenyl dibenzimidazole tetrasulfonate (10% or less, expressed as acid), bis ethylhexyloxyphenol methoxyphenol triazine (10% or less), methylene bisbenzotriazolyl tetramethylbutylphenol (10% or less, also called TINOSORB M or Bisoctrizole), and bisethylhexyloxyphenol methoxyphenyl triazine. (10% or less, also called TINOSORB S or Bemotrizinol).

All of the above described UV filters are commercially available. For example, suitable commercially available organic UV filters are identified by trade name and supplier in Table I below:

TABLE I

| CTFA Name | Trade Name | Supplier |
| --- | --- | --- |
| benzophenone-3 | UVINUL M-40 | BASF Chemical Co. |
| benzophenone-4 | UVINUL MS-40 | BASF Chemical Co. |
| benzophenone-8 | SPECTRA-SORB UV-24 | American Cyanamid |
| DEA-methoxycinnamate | BERNEL HYDRO | Bernel Chemical |
| diethylamino hydroxybenzoyl hexyl benzoate | UVINUL A-PLUS | BASF Chemical Co. |
| diethylhexyl butamido triazone | UVISORB HEB | 3V-Sigma |
| disodium phenyl dibenzylimidazole | NEO HELIOPAN AP | Symrise |
| ethyl dihydroxypropyl-PABA | AMERSCREEN P | Amerchol Corp. |
| glyceryl PABA | NIPA G.M.P.A. | Nipa Labs. |
| homosalate | KEMESTER HMS | Humko Chemical |
| menthyl anthranilate | SUNAROME UVA | Felton Worldwide |
| octocrylene | UVINUL N-539 | BASF Chemical Co. |
| octyl dimethyl PABA | AMERSCOL | Amerchol Corp. |
| octyl methoxycinnamate | PARSOL MCX | Bernel Chemical |
| PABA | PABA | National Starch |
| 2-phenylbenzimidazole-5-sulphonic acid | EUSOLEX 6300 | EM Industries |
| TEA salicylate | SUNAROME W | Felton Worldwide |
| 2-(4-methylbenzildene)-camphor | EUSOLEX 6300 | EM Industries |
| benzophenone-1 | UVINUL 400 | BASF Chemical Co. |
| benzophenone-2 | UVINUL D-50 | BASF Chemical Co. |
| benzophenone-6 | UVINUL D-49 | BASF Chemical Co. |
| benzophenone-12 | UVINUL 408 | BASF Chemical Co. |
| 4-isopropyl dibenzoyl methane | EUSOLEX 8020 | EM Industries |
| butyl methoxy dibenzoyl methane | PARSOL 1789 | Givaudan Corp. |

TABLE I-continued

| CTFA Name | Trade Name | Supplier |
| --- | --- | --- |
| etocrylene | UVINUL N-35 | BASF Chemical Co. |
| methylene bisbenzotriazolyl tetramethylbutylphenol | TINOSORB M | Ciba Specialty Chemicals |
| bisethylhexyloxyphenol methoxyphenyl triazine. | TINOSORB S | Ciba Specialty Chemicals |

Commonly-assigned U.S. Pat. Nos. 6,485,713 and 6,537,529, the disclosures of which are hereby incorporated herein by reference, describe compositions and methods for increasing the photostability of photoactive compounds in a sunscreen composition, e.g., by the addition of polar solvents to the oil phase of a composition. By increasing the polarity of the oil phase of a sunscreen composition including the alkoxy crylenes described herein, e.g., methoxy crylene, the stability of the sunscreen composition is surprisingly increased in comparison to octocrylene. In the sunscreen compositions described herein, preferably, one or more of a highly polar solvent is present in the oil-phase of the composition. Preferably, a sufficient amount of a polar solvent is present in the sunscreen composition to raise the dielectric constant of the oil-phase of the composition to a dielectric constant of at least about 7, preferably at least about 8. With or without the highly polar solvent in the oil phase, the methoxy crylene molecules described herein yield unexpected photostability in comparison to octocrylene.

A photoactive compound can be considered stable when, for example, after 30 MED irradiation the photoactive compound has retained at least about 90% of its original absorbance at a wavelength, or over a range of wavelengths of interest (e.g., the wavelength at which a photoactive compound has a peak absorbance, such as 350-370 nm for Avobenzone). Likewise, a sunscreen composition can include a plurality of photoactive compounds and a sunscreen composition, as a whole, can be considered stable when, for example, after 30 MED irradiation the sunscreen composition has retained at least about 90% of its original absorbance at one or more wavelengths of interest (e.g., at or near the peak absorbance wavelength of the primary photoactive compound).

In accordance with one important embodiment, an alkoxycrylene of formula (I) is combined in a sunscreen or dermatological formulation with a water soluble UV filter compound and/or a broad-band filter compound and optionally, but preferably, together with a dibenzoylmethane derivative and/or a dialkyl naphthalate.

Advantageous water-soluble UV filter substances for the purposes of the present invention are sulfonated UV filters, in particular:

phenylene-1,4-bis(2-benzimidazyl)-3,3'-5,5'-tetrasulfonic acid, which has the following structure:

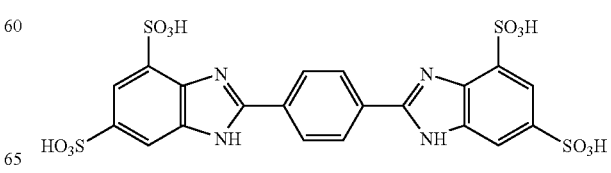

and its salts, especially the corresponding sodium, potassium or triethanolammonium salts, in particular phenylene-1,4-bis (2-benzimidazyl)-3,3'-5,5'-tetrasulfonic acid bissodium salt

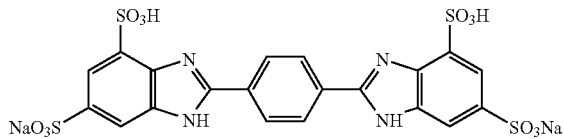

with the INCI name disodium phenyl dibenzimidazole tetrasulfonate (CAS No.: 180898-37-7), which is obtainable for example under the proprietary name Neo Heliopan A P from Haarmann & Reimer.

Further advantageous sulfonated UV filters for the purposes of the present invention are the salts of 2-phenylbenzimidazole-5-sulfonic acid, such as its sodium, potassium or its triethanolammonium salts, and the sulfonic acid itself

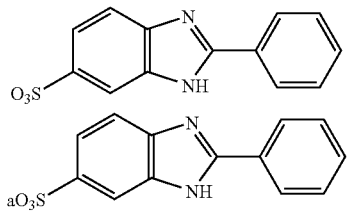

with the INCI name phenylbenzimidazole sulfonic acid (CAS No. 27503-81-7), which is obtainable for example under the proprietary name Eusolex 232 from Merck or under Neo Heliopan Hydro from Haarmann & Reimer.

Further advantageous water-soluble UV-B and/or broadband filter substances for the purposes of the present invention are, for example, sulfonic acid derivatives of 3-benzylidenecamphor, such as, for example, 4-(2-oxo-3-bornylidenemethyl)benzene-sulfonic acid, 2-methyl-5-(2-oxo-3-bornylidenemethyl)sulfonic acid and the salts thereof.

The total amount of one or more water-soluble UV filter substances in the finished cosmetic or dermatological preparations is advantageously chosen from the range 0.01% by weight to 20% by weight, preferably from 0.1 to 10% by weight, in each case based on the total weight of the preparations.

In accordance with another important embodiment, an alkoxycrylene of formula (I) is combined in a sunscreen or dermatological formulation with a hydroxybenzophenone compound and/or a broad-band filter compound and optionally, but preferably, together with a dibenzoylmethane derivative and/or a dialkyl naphthalate.

With an alkoxycrylene, it is possible to completely dispense with the use of other UV stabilizers, in particular the use of ethylhexyl-2-cyano-3,3-diphenylacrylate(octocrylene) or 4-methylbenzylidenecamphor.

Hydroxybenzophenones are characterized by the following structural formula:

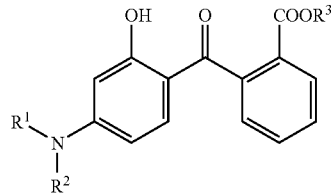

where $R^1$ and $R^2$ independent of one another are hydrogen, $C_1$-$C_{20}$-alkyl, $C_3$-$C_{10}$-cycloalkyl or $C_3$-$C_{10}$-cyloalkenyl, wherein the substituents $R^1$ and $R^2$ together with the nitrogen atom to which they are bound can form a 5- or 6-ring and $R^3$ is a $C_1$-$C_{20}$ alkyl radical.

A particularly advantageous hydroxybenzophenone is the 2-(4'-diethylamino-2'-hydroxybenzoyl)benzoic acid hexyl ester (also: aminobenzophenone) which is characterized by the following structure:

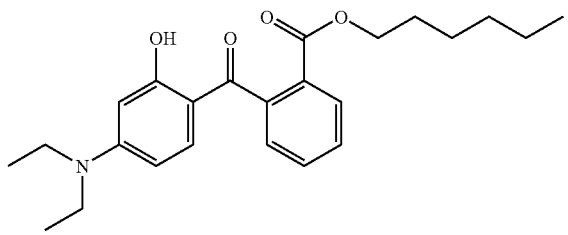

and is available from BASF under the Uvinul A Plus.

According to the invention, cosmetic or dermatological preparations contain 0.1 to 20% by weight, advantageously 0.1 to 15% by weight, very particularly preferred 0.1 to 10% by weight, of one or more hydroxybenzophenones.

Within the scope of the present invention, dialkyl naphthalates for which $R^1$ and/or $R^2$ represent branched alkyl groups with 6 to 10 carbon atoms are advantageous. Within the scope of the present invention diethylhexyl naphthalate is very particularly preferred which is available, e.g., under the trade name Hallbrite TQ™ from CP Hall or Corapan TQ™ from H&R.

According to one embodiment of the invention cosmetic or dermatological preparations advantageously contain 0.001 to 30% by weight, preferably 0.01 to 20% by weight, very particularly preferred 0.5 to 15% by weight, of one or more dialkyl naphthalates.

The cosmetic or dermatological light-protection formulations according to the invention can be composed as usual and be used for cosmetic or dermatological light-protection, furthermore for the treatment, care and cleansing of the skin and/or hair and as a cosmetic product in decorative cosmetics.

In accordance with another important embodiment, an alkoxycrylene of formula (I) is combined in a sunscreen or dermatological formulation with a benzotriazole derivatives compound and/or a broad-band filter compound and optionally, but preferably, together with a dibenzoylmethane derivative and/or a dialkyl naphthalate.

An advantageous benzotriazole derivative is 2,2'-methylenebis(6-(2H-benzotriazol-2-yl)-4-(1,1,3,3-tetramethylbutyl)phenol), which has the chemical structural formula

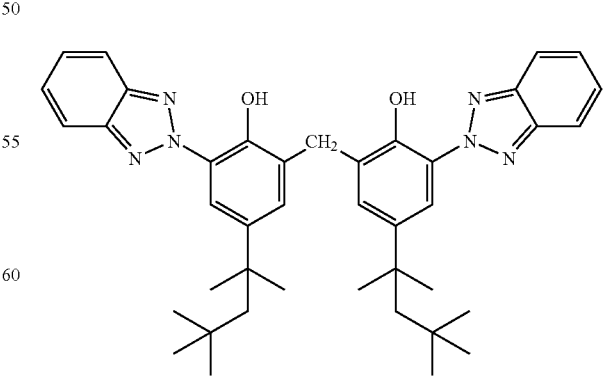

(INCI: bisoctyltriazole). It is obtainable under the proprietary name Tinosorb® from CIBA-Chemikalien GmbH and is distinguished by good UV absorption properties. The disadvantage of this substance is the characteristic of forming imperceptibly thin films on the skin which have unpleasant tactile properties.

Another disadvantage is that such benzotriazole derivatives show only inadequate solubility, if any, in conventional oil components. Well-known solvents can dissolve only up to a maximum of 15% by weight of these compounds, which usually corresponds to a concentration of about 1 to 1.5% by weight of dissolved (=active) filter substance in the complete cosmetic or dermatological preparation.

One disadvantage of the prior art is accordingly that generally only comparatively low sun protection factors have been achievable with these filter substances because their solubility or dispersibility in the formulations is too low, i.e. they can be satisfactorily incorporated into such formulations only with difficulty or not at all.

Even if it is also possible in principle to achieve a certain UV protection when the solubility is limited, another problem frequently occurs, that is recrystallization.

Substances of low solubility in particular recrystallize comparatively rapidly, which may be induced by fluctuations in temperature or other influences. Uncontrolled recrystallization of an essential ingredient of a preparation such as a UV filter has, however, extremely disadvantageous effects on the properties of the given preparation and, not least, on the desired light protection.

In accordance with another embodiment, the alkoxycrylene-containing compositions described herein can contain an increased content of unsymmetrically substituted triazine derivatives when combined together with an alkoxycrylene of formula (I) to obtain an increased sun protection factor.

It was, however, surprising and not predictable for the skilled worker that the disadvantages of the prior art are remedied by active ingredient combinations effective for light protection and composed of (a) one or more UV filter substances selected from the group of benzotriazole derivatives;
(b) an alkoxycrylene of formula (I); and optionally
(c) one or more dialkyl naphthalates having the structural formula:

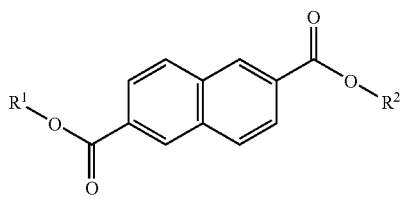

in which $R^1$ and $R^2$ are, independently of one another, selected from the group of branched and unbranched alkyl groups having 6 to 24 carbon atoms.

Particularly advantageous light protection filters for the purpose of this embodiment of the present invention include a benzotriazole compound having a structural formula:

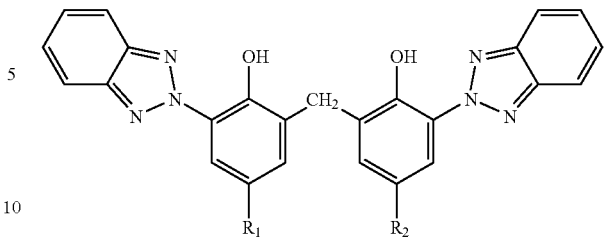

where $R_1$ and $R_2$ are, independently of one another, selected from the group of branched or unbranched $C_1$-$C_{18}$-alkyl radicals, of $C_5$-$C_{12}$-cycloalkyl or aryl radicals which are optionally substituted by one or more $C_1$-$C_4$ alkyl groups.

The preferred benzotriazole derivative is 2,2'-methylenebis(6-(2H-benzotriazol-2-yl)-4-(1,1,3,3-tetramethylbutyl)phenol) which is characterized by the chemical structural formula:

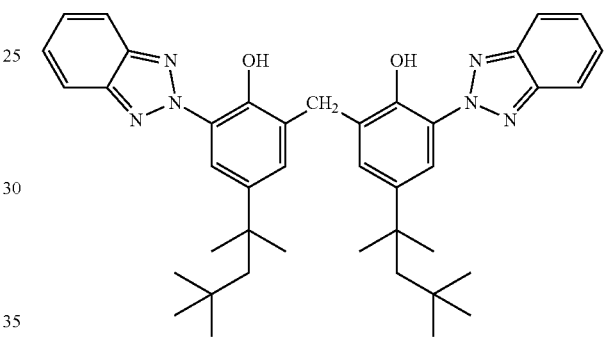

An advantageous broadband filter for the purpose of the present invention is moreover 2-(2H-benzotriazol-2-yl)-4-methyl-6-[2-methyl-3-[1,3,3,3-tetramethyl-1-[(trimethyl-silyl)oxy]disiloxanyl]propyl]phenol (CAS No.: 155633-54-8) with the INCI name drometrizole trisiloxane, which is characterized by the chemical structural formula

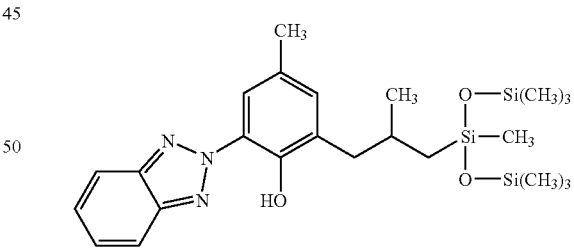

The total amount of one or more benzotriazole derivatives, in particular of 2,2'-methylenebis(6-(2H-benzotriazol-2-yl)-4-(1,1,3,3-tetramethylbutyl)phenol) and/or 2-(2H-benzotriazol-2-yl)-4-methyl-6-[2-methyl-3-[1,3,3,3-tetramethyl-1-[(trimethylsilyl)oxy]disiloxanyl]propyl]phenol, in the finished cosmetic or dermatological preparations is advantageously chosen from the range from 0.1 to 15.0% by weight, preferably 0.5 to 10.0% by weight, based on the total weight of the preparations.

The cosmetic or dermatological light protection formulations of the invention may have conventional compositions and be used for cosmetic or dermatological light protection and for the treatment, care and cleansing of skin and/or the hair and as a make-up product in decorative cosmetics.

For use, the cosmetic and dermatological preparations are applied to the skin and/or the hair in a sufficient quantity in the manner customary for cosmetics.

Cosmetic and dermatological preparations according to the invention can comprise cosmetic auxiliaries such as those conventionally used in such preparations, e.g. preservatives, bactericides, perfumes, antifoams, dyes, pigments which have a coloring effect, thickeners, moisturizers and/or humectants, fats, oils, waxes or other conventional constituents of a cosmetic or dermatological formulation, such as alcohols, polyols, polymers, foam stabilizers, electrolytes, organic solvents or silicone derivatives.

An additional content of antioxidants is generally preferred. According to the invention, favorable antioxidants which can be used are any antioxidants suitable or conventional for cosmetic and/or dermatological applications.

The antioxidants are particularly advantageously chosen from the group consisting of amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. .alpha.-carotene, .beta.-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, .gamma.-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximine) in very low tolerated doses (e.g. pmol to .mu.mol/kg), and also (metal) chelating agents (e.g. .alpha.-hydroxy fatty acids, palmitic acid, phytic acid, lactoferrin), .alpha.-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. .gamma.-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of gum benzoin, rutinic acid and derivatives thereof, alpha.-glycosylrutin, ferulic acid, furfurylideneglucitol, carnosine, butylhydroxytoluene, butylhydroxyanisole, nordihydroguaiaretic acid, trihydroxybutyro-phenone, uric acid and derivatives thereof, mannose and derivatives thereof, zinc and derivatives thereof (e.g. ZnO, ZnSO$_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

In accordance with another important embodiment, an alkoxycrylene of formula (I) is combined in a sunscreen or dermatological formulation with hydrophilic skincare active ingredients and/or a broad-band filter compound and optionally, but preferably, together with a dibenzoylmethane derivative.

Advantageous hydrophilic active ingredients which (individually or in any combinations with one another) are stabilized by their use together with an alkoxycrylene according to the invention include those listed below:

biotin; carnitine and derivatives; creatine and derivatives; folic acid; pyridoxine; niacinamide; polyphenols (in particular flavonoids, very particularly alpha-glucosylrutin); ascorbic acid and derivatives; Hamamelis; Aloe Vera; panthenol; amino acids.

Particularly advantageous hydrophilic active ingredients for the purposes of the present invention are also water-soluble antioxidants, such as, for example, vitamins.

The amount of hydrophilic active ingredients (one or more compounds) in the preparations is preferably 0.0001 to 10% by weight, particularly preferably 0.001 to 5% by weight, based on the total weight of the preparation.

Particularly advantageous preparations are also obtained when antioxidants are used as additives or active ingredients. According to the invention, the preparations advantageously comprise one or more antioxidants. Favorable, but nevertheless optional antioxidants which may be used are all antioxidants customary or suitable for cosmetic and/or dermatological applications.

The amount of antioxidants (one or more compounds) in the preparations is preferably 0.001 to 30% by weight, particularly preferably 0.05 to 20% by weight, in particular 0.1 to 10% by weight, based on the total weight of the preparation.

If vitamin E and/or derivatives thereof are the antioxidant or antioxidants, it is advantageous to choose their respective concentrations from the range from 0.001 to 10% by weight, based on the total weight of the formulation.

If vitamin A or vitamin A derivatives, or carotenes or derivatives thereof are the antioxidant or antioxidants, it is advantageous to choose their respective concentrations from the range from 0.001 to 10% by weight, based on the total weight of the formulation.

It is particularly advantageous when the cosmetic preparations according to the present invention comprise further cosmetic or dermatological active ingredients, preferred active ingredients being antioxidants which can protect the skin against oxidative stress.

Advantageous further active ingredients are natural active ingredients and/or derivatives thereof, such as e.g. ubiquinones, retinoids, carotenoids, creatine, taurine and/or .beta.-alanine.

Formulations according to the invention, which comprise e.g. known antiwrinkle active ingredients, such as flavone glycosides (in particular .alpha.-glycosylrutin), coenzyme Q10, vitamin E and/or derivatives and the like, are particularly advantageously suitable for the prophylaxis and treatment of cosmetic or dermatological changes in skin, as arise, for example, during skin aging (such as, for example, dryness, roughness and formation of dryness wrinkles, itching, reduced refatting (e.g. after washing), visible vascular dilations (teleangiectases, couperosis), flaccidity and formation of wrinkles and lines, local hyperpigmentation, hypopigmentation and abnormal pigmentation (e.g. age spots), increased susceptibility to mechanical stress (e.g. cracking) and the like). In addition, they are advantageously suitable against the appearance of dry or rough skin.

In accordance with still another important embodiment, an alkoxycrylene of formula (I) is combined in a sunscreen or dermatological formulation with particulate UV filter substances and/or a broad-band filter compound and optionally, but preferably, together with a dibenzoylmethane derivative and/or a dialkyl naphthalate.

Preferred particulate UV filter substances for the purposes of the present invention are inorganic pigments, especially metal oxides and/or other metal compounds which are slightly soluble or insoluble in water, especially oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and mixtures of such oxides, and the sulfate of barium ($BaSO_4$).

Zinc oxides for the purposes of the present invention may also be used in the form of commercially available oily or aqueous predispersions. Zinc oxide particles and predispersions of zinc oxide particles which are suitable according to the invention are distinguished by a primary particle size of <300 nm and can be obtained under the following proprietary names from the stated companies:

| Proprietary name | Coating | Manufacturer |
|---|---|---|
| Z-Cote HP1 | 2% Dimethicone | BASF |
| Z-Cote | / | BASF |
| ZnO NDM | 5% Dimethicone | H&R |
| ZnO Neutral | / | H&R |
| MZ-300 | / | Tayca Corporation |
| MZ-500 | / | Tayca Corporation |
| MZ-700 | / | Tayca Corporation |
| MZ-303S | 3% Methicone | Tayca Corporation |
| MZ-505S | 5% Methicone | Tayca Corporation |
| MZ-707S | 7% Methicone | Tayca Corporation |
| MZ-303M | 3% Dimethicone | Tayca Corporation |
| MZ-505M | 5% Dimethicone | Tayca Corporation |
| MZ-707M | 7% Dimethicone | Tayca Corporation |
| Z-Sperse Ultra | ZnO (>=56%)/Ethylhexyl Hydroxystearate Benzoate/ Dimethicone/Cyclomethicone | Collaborative Laboratories |
| Samt-UFZO-450/D5 (60%) | ZnO (60%)/Cyclomethicone/ Dimethicone | Miyoshi Kasei |

Particularly preferred zinc oxides for the purposes of the invention are Z-Cote HP1 and Z-Cote from BASF and zinc oxide NDM from Haarmann & Reimer.

Titanium dioxide pigments of the invention may be in the form of both the rutile and anatase crystal modification and may for the purposes of the present invention advantageously be surface-treated ("coated"), the intention being for example to form or retain a hydrophilic, amphiphilic or hydrophobic character. This surface treatment may consist of providing the pigments by processes known per se with a thin hydrophilic and/or hydrophobic inorganic and/or organic layer. The various surface coatings may for the purposes of the present invention also contain water.

Inorganic surface coatings for the purposes of the present invention may consist of aluminum oxide ($Al_2O_3$), aluminum hydroxide $Al(OH)_3$ or aluminum oxide hydrate (also: alumina, CAS No.: 1333-84-2), sodium hexametaphosphate $(NaPO_3)_6$, sodium metaphosphate $(NaPO_3)_n$, silicon dioxide ($SiO_2$) (also: silica, CAS No.: 7631-86-9), or iron oxide ($Fe_2O_3$). These inorganic surface coatings may occur alone, in combination and/or in combination with organic coating materials.

Organic surface coatings for the purposes of the present invention may consist of vegetable or animal aluminum stearate, vegetable or animal stearic acid, lauric acid, dimethylpolysiloxane (also: dimethicones), methylpolysiloxane (methicones), simethicones (a mixture of dimethylpolysiloxane with an average chain length of from 200 to 350 dimethylsiloxane units and silica gel) or alginic acid. These organic surface coatings may occur alone, in combination and/or in combination with inorganic coating materials.

Coated and uncoated titanium dioxides of the invention may be used in the form of commercially available oily or aqueous predispersions. It may be advantageous to add dispersion aids and/or solubilization mediators.

Suitable titanium dioxide particles and predispersions of titanium dioxide particles for the purposes of the present invention are obtainable under the following proprietary names from the stated companies:

| Proprietary name | Coating | Additional ingredients of the predispersion | Manufacturer |
|---|---|---|---|
| MT-150W | None | — | Tayca Corporation |
| MT-150A | None | — | Tayca Corporation |
| MT-500B | None | — | Tayca Corporation |
| MT-600B | None | — | Tayca Corporation |
| MT-100TV | Aluminum hydroxide Stearic acid | — | Tayca Corporation |
| MT-100Z | Aluminum hydroxide Stearic acid | — | Tayca Corporation |
| MT-100T | Aluminum hydroxide Stearic acid | — | Tayca Corporation |
| MT-500T | Aluminum hydroxide Stearic acid | — | Tayca Corporation |
| MT-100S | Aluminum hydroxide Lauric acid | — | Tayca Corporation |
| MT-100F | Stearic acid Iron oxide | — | Tayca Corporation |
| MT-100SA | Alumina Silica | — | Tayca Corporation |
| MT-500SA | Alumina Silica | — | Tayca Corporation |
| MT-600SA | Alumina Silica | — | Tayca Corporation |
| MT-100SAS | Alumina Silica Silicone | — | Tayca Corporation |

-continued

| Proprietary name | Coating | Additional ingredients of the predispersion | Manufacturer |
|---|---|---|---|
| MT-500SAS | Alumina Silica Silicone | — | Tayca Corporation |
| MT-500H | Alumina | — | Tayca Corporation |
| MT-100AQ | Silica Aluminum hydroxide Alginic acid | — | Tayca Corporation |
| Eusolex T | Water Simethicone | — | Merck KgaA |
| Eusolex T-2000 | Alumina Simethicone | — | Merck KgaA |
| Eusolex T-Olio F | Silica Dimethylsilate Water | $C_{12-15}$ Alkylbenzoate Calcium Polyhydroxystearate Silica Dimethylsilate | Merck KgaA |
| Eusolex T-Olio P | Water Simethicone | Octyl Palmitate PEG-7 Hydrogenated Castor Oil Sorbitan Oleate Hydrogenated Castor Oil Beeswax Stearic acid | Merck KgaA |
| Eusolex T-Aqua | Water Alumina Sodium metaphosphate | Phenoxyethanol Sodium Methylparabens Sodium metaphosphate | Merck KgaA |
| Eusolex T-45D | Alumina Simethicone | Isononyl Isononanuate Polyglyceryl Ricinoleate | Merck KgaA |
| Kronos 1171 (Titanium dioxide 171) | None | — | Kronos |
| Titanium dioxide P25 | None | — | Degussa |
| Titanium dioxide T805 | Octyltrimethylsilane (Uvinul $TiO_2$) | — | Degussa |
| UV-Titan X610 | Alumina Dimethicone | — | Kemira |
| UV-Titan X170 | Alumina Dimethicone | — | Kemira |
| UV-Titan X161 | Alumina Silica Stearic acid | — | Kemira |
| UV-Titan M210 | Alumina | — | Kemira |
| UV-Titan M212 | Alumina | Glycerol | Kemira |
| UV-Titan M262 | Alumina Silicone | — | Kemira |
| UV-Titan M160 | Alumina Silica Stearic acid | — | Kemira |
| Tioveil AQ 10PG | Alumina Silica | Water Propylene glycol | Solaveil Uniquema |
| Mirasun TiW 60 | Alumina Silica | Water | Rhone-Poulenc |

The titanium dioxides of the invention are distinguished by a primary particle size between 10 nm to 150 nm.

Titanium dioxides particularly preferred for the purposes of the present invention are MT-100 Z and MT-100 TV from Tayca Corporation, Eusolex T-2000 from Merck and titanium dioxide T 805 from Degussa.

Further advantageous pigments are latex particles. Latex particles which are advantageous according to the invention are described in the following publications: U.S. Pat. No. 5,663,213 and EP 0 761 201. Particularly advantageous latex particles are those formed from water and styrene/acrylate copolymers and available for example under the proprietary name "Alliance SunSphere" from Rohm & Haas.

An advantageous organic pigment for the purposes of the present invention is 2,2'-methylenebis(6-(2H-benzotriazol-2-yl)-4-(1,1,3,3-tetramethylbutyl-)phenol) (INCI: bis-octyltriazol), which is obtainable under the proprietary name Tinosorb® M from CIBA-Chemikalien GmbH.

It is particularly advantageous for the purposes of the present invention for particulate UV filter substances which are not already in the form of a predispersion first to be dispersed in one or more dialkyl naphthalates of the invention and for this basic dispersion then to be further processed. Whereas auxiliaries which may enter into unwanted interactions with other substances of the cosmetic or dermatological formulation are usually added for stabilization to commercially available predispersions, it is astonishingly possible to dispense with the addition of such stabilizers when preparing basic dispersions of the invention.

The total amount of one or more water-soluble UV filter substances in the finished cosmetic or dermatological preparations is advantageously chosen from the range 0.01% by weight to 20% by weight, preferably from 0.1 to 10% by weight, in each case based on the total weight of the preparations.

In accordance with still another important embodiment, an alkoxycrylene of formula (I) is combined in a sunscreen or dermatological formulation with asymmetrically substituted triazine UV filter compounds and/or a broad-band filter compound and optionally, but preferably, together with a dibenzoylmethane derivative.

Asymmetrically substituted triazine derivatives display a good light protection effect. Their main disadvantage is, however, that their solubility is low in conventional oil components. Well-known solvents can dissolve only up to a maximum of 15% by weight of these compounds, which usually corresponds to a concentration of about 1 to 1.5% by weight of dissolved (=active) filter substance in the complete cosmetic or dermatological preparation.

One disadvantage of the prior art is accordingly that generally only comparatively low sun protection factors have been achievable with these filter substances because their solubility or dispersibility in the formulations is too low, i.e. they can be satisfactorily incorporated into such formulations only with difficulty or not at all.

Even if it is also possible in principle to achieve a certain UV protection when the solubility is limited, another problem frequently occurs, that is recrystallization. Substances of low solubility in particular recrystallize comparatively rapidly, which may be induced by fluctuations in temperature or other influences. Uncontrolled recrystallization of an essential ingredient of a preparation such as a UV filter has, however, extremely disadvantageous effects on the properties of the given preparation and, not least, on the desired light protection.

It was an object of the present invention to obtain in a simple manner preparations which are distinguished by an increased content of asymmetrically substituted triazine derivatives and a correspondingly high sun protection factor.

Disadvantages of the prior art are remedied by active ingredient combinations effective for light protection and composed of:
(a) one or more UV filter substances selected from the group of asymmetrically substituted triazine derivatives, and
(b) one or more alkoxycrylenes having the structural formula (I); and
(c) optionally a dibenzoylmethane derivative and/or a dialkyl naphthalate.

Advantageous asymmetrically substituted s-triazine derivatives within the meaning of this embodiment of the present invention are, for example, those described in EP-A-570 838, whose chemical structure is represented by the generic formula

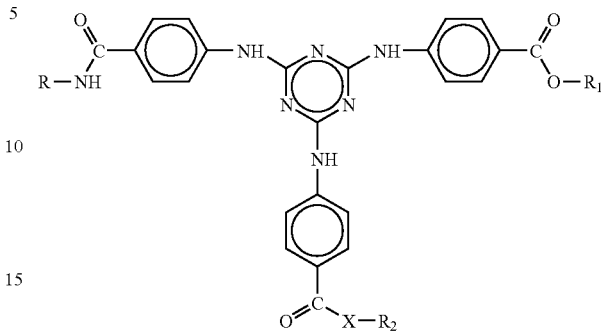

where
R is a branched or unbranched $C_1$-$C_{18}$-alkyl radical, a $C_5$-$C_{12}$-cycloalkyl radical, optionally substituted by one or more $C_1$-$C_4$-alkyl groups, and
X is an oxygen atom or an NH group,
$R_1$ is a branched or unbranched $C_1$-$C_{18}$-alkyl radical, a $C_5$-$C_{12}$-cycloalkyl radical, optionally substituted by one or more $C_1$-$C_4$-alkyl groups, or a hydrogen atom, an alkali metal atom, an ammonium group or a group of the formula

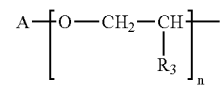

in which
A is a branched or unbranched $C_1$-$C_{18}$-alkyl radical, a $C_5$-$C_{12}$-cycloalkyl or aryl radical, optionally substituted by one or more $C_1$-$C_4$-alkyl groups,
$R_3$ is a hydrogen atom or a methyl group,
n is a number from 1 to 10,
$R_2$ is a branched or unbranched $C_1$-$C_{18}$-alkyl radical, a $C_5$-$C_{12}$-cycloalkyl radical, optionally substituted by one or more $C_1$-$C_4$-alkyl groups, and
if X is the NH group,
a branched or unbranched $C_1$-$C_{18}$-alkyl radical, a $C_5$-$C_{12}$-cycloalkyl radical, optionally substituted by one or more $C_1$-$C_4$-alkyl groups, or a hydrogen atom, an alkali metal atom, an ammonium group or a group of the formula

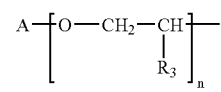

in which
A is a branched or unbranched $C_1$-$C_{18}$-alkyl radical, a $C_5$-$C_{12}$-cycloalkyl or aryl radical, optionally substituted by one or more $C_1$-$C_4$-alkyl groups,
$R_3$ is a hydrogen atom or a methyl group,
n is a number from 1 to 10, if X is an oxygen atom.

In a preferred form of this triazine embodiment, the compositions are sunscreen, cosmetic or dermatological formulations that include a content of least one asymmetrically substituted s-triazine selected from the group of substances having the following structural formula:

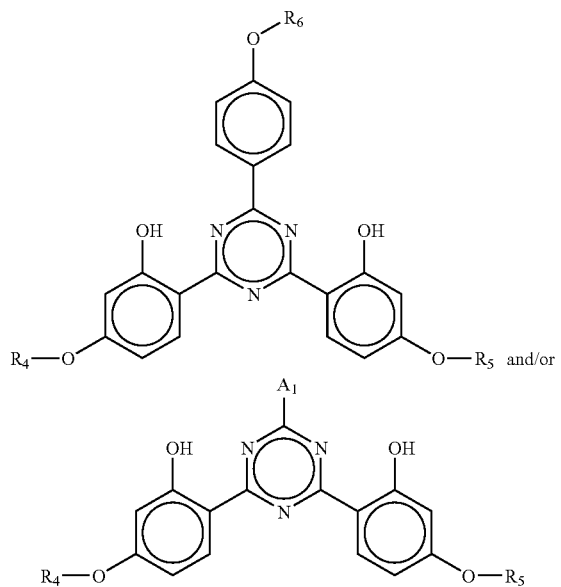

All the bisresorcinyltriazines, are advantageous for this embodiment of the purpose of the present invention. $R_4$ and $R_5$ are very particularly advantageously selected from the group of branched or unbranched alkyl groups of 1 to 18 carbon atoms. The alkyl groups may also again advantageously be substituted by silyloxy groups.

$A_1$ is advantageously a substituted homocyclic or heterocyclic aromatic five-membered ring or six-membered ring.

The following compounds are very particularly advantageous:

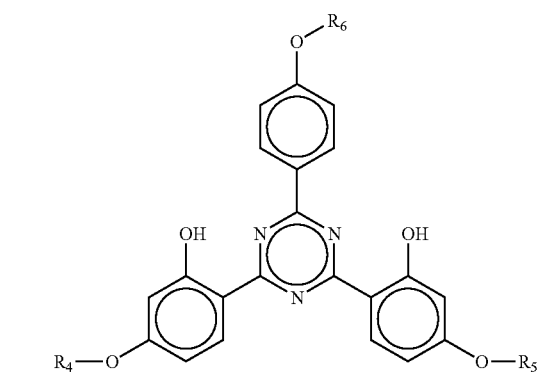

where $R_6$ is a hydrogen atom or a branched or unbranched alkyl group with 1 to 10 carbon atoms, in particular 2,4-bis{[4-(2-ethylhexyloxy)-2-hydroxyl]phenyl}-6-(4-methoxyphenyl)-1,3,5-triazine (INCI: aniso triazine), which is obtainable under the proprietary name Tinosorb® S from CIBA-Chemikalien GmbH and is characterized by the following structure:

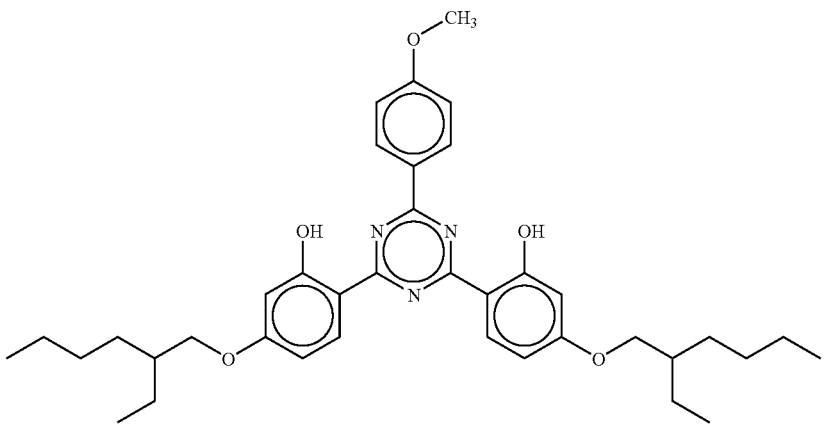

Also advantageous is 2,4-bis{[4-(3-sulfonato-2-hydroxypropyloxy)-2-hydroxyl]phenyl}-6-(4-methoxy phenyl)-1,3,5-triazine sodium salt, which is characterized by the following structure:

Also advantageous is 2,4-bis{[4-(3-(2-propyloxy)-2-hydroxypropyloxy)-2-hydroxyl]phenyl}-6-[4-(ethoxycarbonyl)phenylamino]-1,3,5-triazine which is characterized by the following structure:

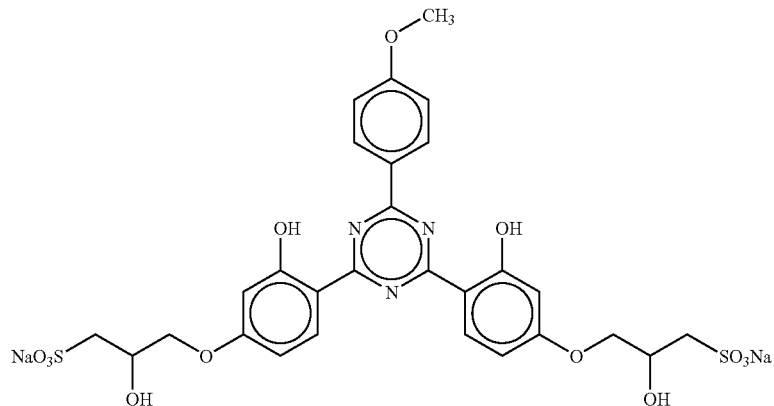

Also advantageous is 2,4-bis{[4-(3-(2-propyloxy)-2-hydroxypropyloxy)-2-hydroxyl]phenyl}-6(4-methoxyphenyl)-1,3,5-triazine, which is characterized by the following structure:

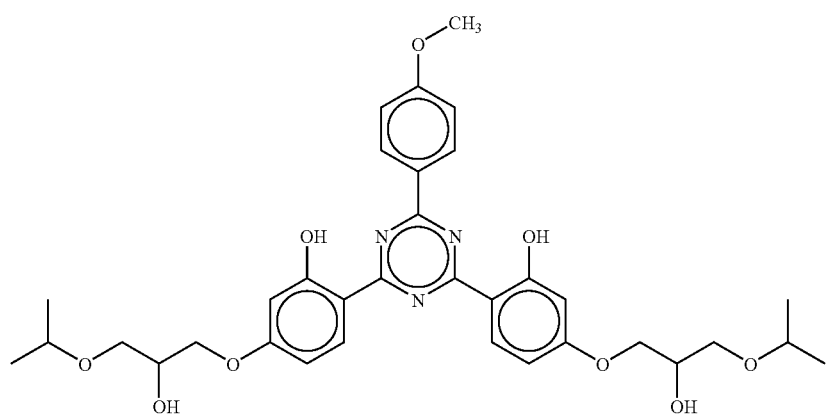

Also advantageous is 2,4-bis{[4-(2-ethylhexyloxy)-2-hydroxyl]phenyl}-6-[4-(2-methoxyethoxycarbonyl)phenylamino]-1,3,5-triazine, which is characterized by the following structure:

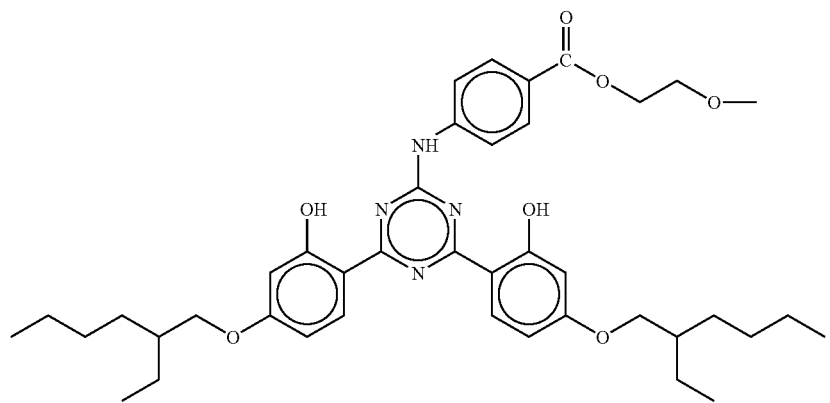

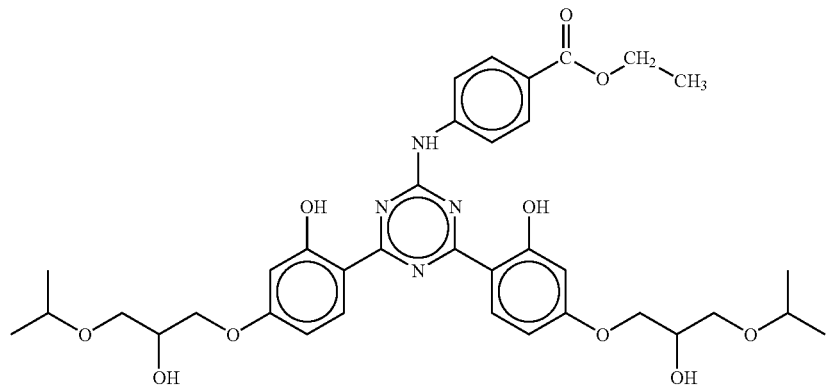

Also advantageous is 2,4-bis{[4-(2-ethylhexyloxy)-2-hydroxyl]phenyl}-6-(1-methylpyrrol-2-yl)1,3,5-triazine, which is characterized by the following structure:

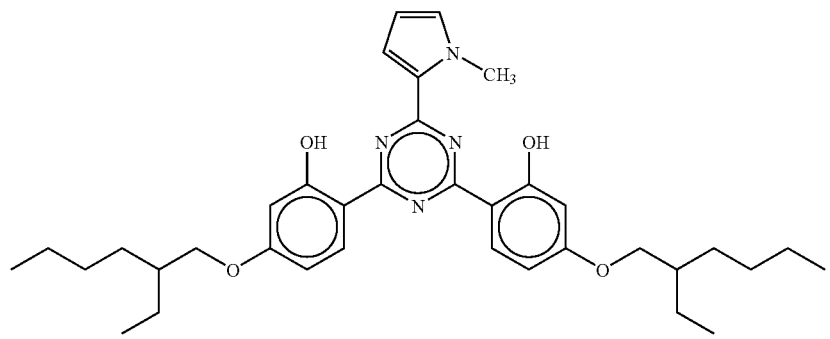

Also advantageous is 2,4-bis{[4-(2-methylpropenyloxy)-2-hydroxyl]phenyl}-6-(4-methoxyphenyl)-1,3,5-triazine, which is characterized by the following structure:

Also advantageous is 2,4-bis{[4-tris(trimethylsiloxysilyl-propyloxy)-2-hydroxyl]phenyl}-6-(4-methoxyphenyl)-1,3,5-triazine, which is characterized by the following structure:

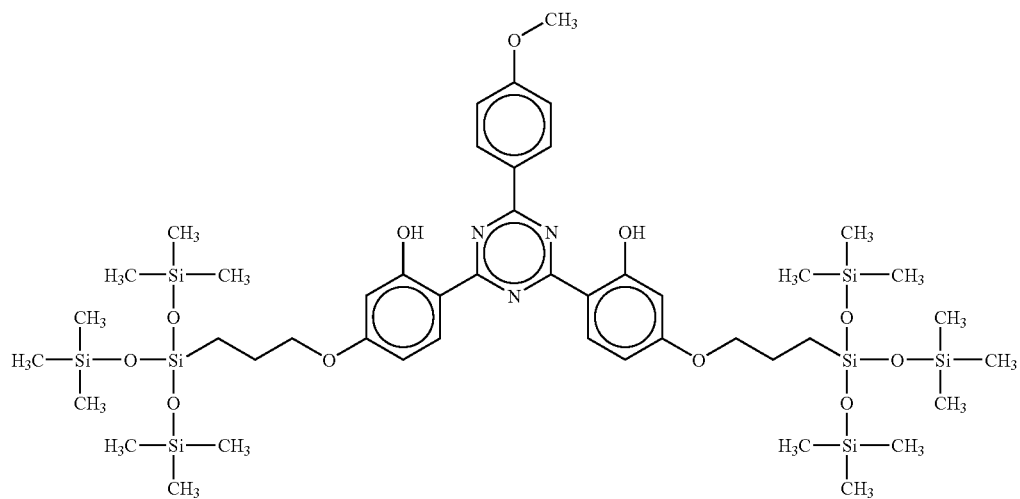

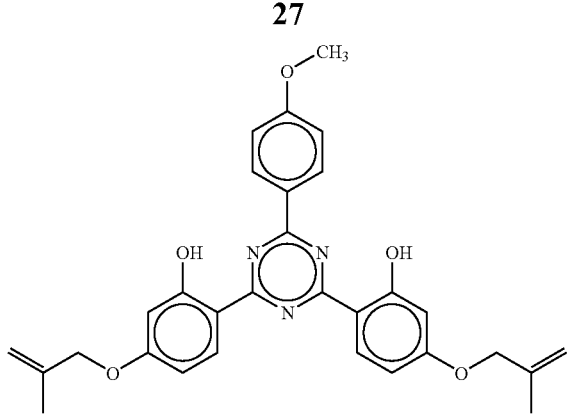

Also advantageous is 2,4-bis{[4-(1',1',1',3',5',5',5'-heptamethylsiloxy-2-methylpropyloxy)-2-hydroxyl]-phenyl}-6-(4-methoxyphenyl)-1,3,5-triazine, which is characterized by the following structure:

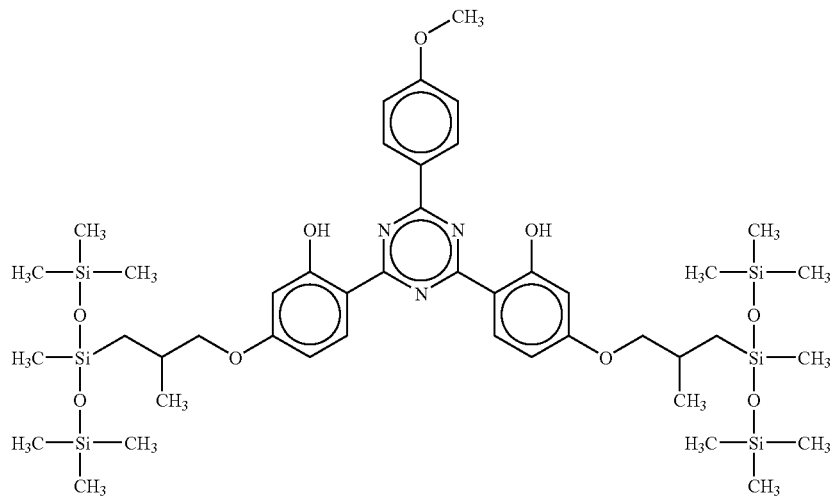

In a particularly preferred embodiment, the present invention relates to cosmetic or dermatological formulations with a content of an asymmetrically substituted s-triazine whose chemical structure is represented by the formula

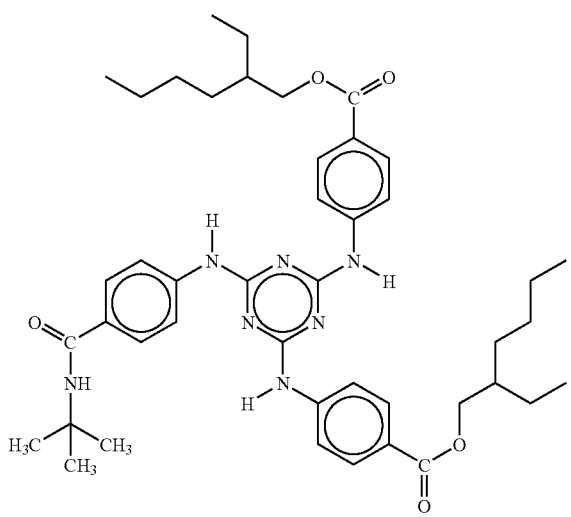

which is also referred to hereinafter as dioctylbutylamidotriazone (INCI) and is obtainable under the proprietary name UVASORB HEB from Sigma 3 V.

The asymmetrically substituted s-triazine derivative(s) of the invention are advantageously incorporated into the oil phase of the cosmetic or dermatological formulations.

The total amount of one or more asymmetrically substituted s-triazine derivatives, in particular of dioctylbutylamidotriazone, in the finished cosmetic or dermatological preparations is advantageously chosen from the range from 0.1 to 15.0% by weight, preferably 0.5 to 10.0% by weight, based on the total weight of the preparations.

The cosmetic or dermatological light protection formulations of the invention may have conventional compositions when used for cosmetic or dermatological light protection and for the treatment, care and cleansing of skin and/or the hair and as a make-up product in decorative cosmetics.

In accordance with one important embodiment, an alkoxycrylene of formula (I) is combined in a sunscreen or dermatological formulation with a lipophilic oxidation or UV-sensitive active ingredients, such as retinoic acid and its derivatives, e.g., tretinoin or isotretinoin and/or a broad-band filter compound and optionally, but preferably, together with a dibenzoylmethane derivative.

Advantageous lipophilic active ingredients which are stabilized in an excellent manner by the use according to the invention are those whose log P value is greater than 3.5. P is the partition coefficient, which is defined as the ratio of the equilibrium concentration of a dissolved substance in a two-phase system which consists of two solvents which are essentially immiscible with one another. These two solvents are, in the present case, n-octanol and water, i.e.

$$P_{ow} = \frac{C_{n\text{-}octanol}}{C_{water}}$$

It is advantageous for the purposes of the present invention to choose the lipophilic active ingredients from the group of ubiquinones and plastoquinones. For the purposes of the present invention, coenzyme Q10, which has a log P value of about 15, is very particularly advantageous.

It was particularly surprising that very advantageous preparations according to the present invention can be obtained when the active ingredient(s) is/are chosen only from the group of ubiquinones.

Further lipophilic active ingredients which are advantageous according to the invention are retinoids (vitamin A acid and/or derivatives thereof) or vitamin A and/or derivatives thereof. The group of retinoids advantageous according to the invention is defined as including all cosmetically and/or pharmaceutically acceptable retinoids, including retinol and its esters, retinal and also retinoic acid (vitamin A acid) and esters thereof. For the purposes of the present invention, retinol (with a log P value of about 7) and retinyl palmitate (with a log P value of about 13) are particularly advantageous.

It was also particularly surprising that very advantageous preparations can be obtained according to the present invention when the active ingredient(s) is/are chosen only from the group of retinoids.

Further lipophilic acid ingredients advantageous according to the invention are carotenoids. For the purposes of the present invention, .beta.-carotene, which has a log P value of 15, for example, is particularly advantageous.

Further lipophilic active ingredients advantageous according to the invention are: lipoic acid and derivatives, vitamin E and derivatives, vitamin F, dioic acid [8-hexadecene-1,16-dicarboxylic acid (CAS number 20701-68-2)]

The amount of lipophilic active ingredients (one or more compounds) in the preparations is preferably 0.0001 to 10% by weight, particularly preferably 0.001 to 5% by weight, based on the total weight of the preparation.

Synthesis of methyl or ethyl 2-cyano-3-(4'-methoxyphenyl)-3-phenylpropenoate (Methyl or Ethyl Methoxycrylene or Methyl or Ethyl MeOcrylene)

This is due to the fact that the water is distilled in form of a mixture, water/acetic acid/toluene.

3. To prevent from loosing the methyl acetate from the reaction mixture, it helps to put a short packed column between Dean-Stark receiver and the flask.

Work-Up:

The reaction mixture is cooled to room temperature and ethyl acetate is added to dissolve all solids before the crude mixture is washed several time with water, to remove acetic acid and salts. The solvents are then removed from the reaction mixture by distillation. The crude solid product is re-crystallized from hot methanol (or toluene/methanol mixture, if such is preferred).

Comments:

The finished product begins to crystallize out from the cooling reaction mixture and thus can be filtered off, but it still is very acidic, so the crystals ought to be washed with water/methanol mixture to wash out any acetic acid and salts residues. Thus obtained the product then can be re-crystallized and the mother liquor can be washed with water, dried, and second crop of the product can be obtained.

Synthesis of Alkyl 2-cyano-3-(4'-methoxyphenyl)-3-phenylpropenoate

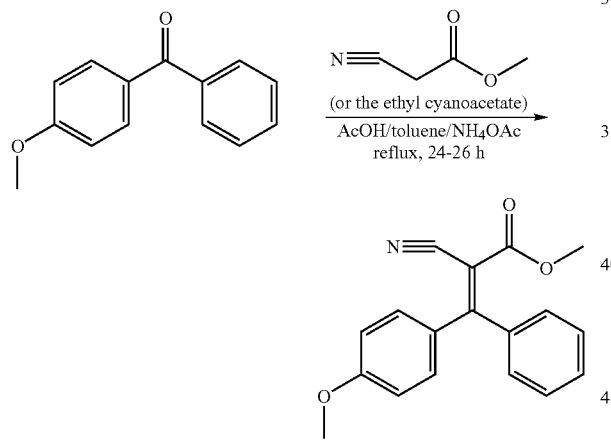

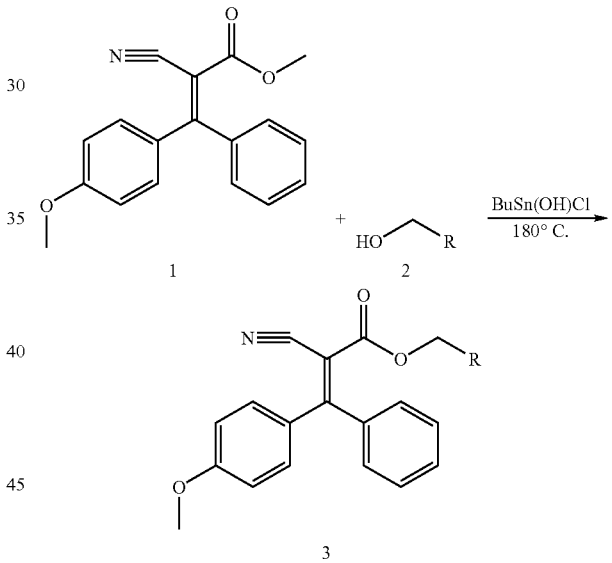

4-Methoxy benzophenone (MW=182.22 g/mole; 500 g; 2.74 mole; 1 mole equivalence) and methyl cyanoacetate (MW=99.09 g/mole; 367.06 g; 3.70 mole; 1.35 mole equivalence) were placed in 1-L 3-neck flask assembled with mechanical stirrer and nitrogen inlet, which provided continuous flow of nitrogen through the reaction mixture (nitrogen is bubbled through the reaction mixture). Next, toluene (1200 ml) and acetic acid (240 ml; ratio of toluene/acetic acid=5/1) are added to the flask followed by ammonium acetate (MW=77.09 g/mole; 21.12 g; 0.274 mole, 0.1 mole equivalence; the catalyst is added 4 times this amount during reaction time). The flask is then assembled with Dean-Stark receiver through which reaction water is being continuously removed.

Comments:
1. Aliquots of the reaction mixture are taken to check the rate of completion of the reaction.
2. The amount of water expected from this reaction is 49.5 ml. However, I collected about 120 ml of water phase.

Reaction Procedure:

Methyl (or ethyl) 2-cyano-3-(4'-methoxyphenyl)-3-phenylpropenoate (900 g, 3.06 mole; MW=293.32), alkyl alcohol (3.84 mole; 1.25 mole equivalence), and Tegokat 250 (0.03% of total batch weight) were placed in 2 L 3-neck round-bottom flask and heated to temperature set at 185 C (365 F), with nitrogen purging it well to remove forming methanol (or ethanol) via the simple distillation setup with packed column.

After 3 h, GC showed full conversion of methyl 2-cyano-3-(4'-methoxyphenyl)-3-phenylpropenoate to the desired product.

Work-Up:

The unreacted alkyl alcohol was completely removed by vacuum distillation. Temperature of the reaction was lowered to 110 C (230 F) and calculated amount (2% of total batch weight) of the SSP (tin removing agent) was added. The product was stirred at this temperature for 2 hours and then filtered hot. Small amount of celite was added right before filtration to enhance the filtration—with celite the filtration was more efficient and faster.

Results:

| Yield of the product | 94% of stoichiometric amount |
|---|---|
| Purity of finished product | 99.81% (area count, GC). |

EXAMPLES

The following compositions (Table I) were prepared according to the procedure indicated in order to show the surprisingly superior photostabilizing effect on avobenzone of the alkoxycrylenes (4.5 wt. %) described herein in comparison to an equimolar amount (2.75 wt. %) of octocrylene. The compound described as "methoxycrylene" had the following formula (IV):

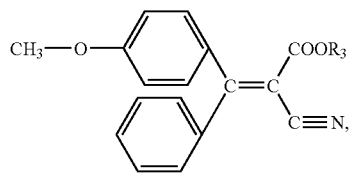

(IV)

wherein $R_3 = C_{20}$

TABLE 1

COMPOSITIONS OF FORMULATIONS TESTED FOR PHOTOSTABILITY

| # | Ingredients | Example 1 (4.5% C20 Methoxycrylene) | Example 2 (POS: 2.75% OC Only) | Example 3 (NEG: No Photo-stabilizer) |
|---|---|---|---|---|
|  | Oil Phase Ingredients |  |  |  |
| 1 | Avobenzone | 3.00% | 3.00% | 3.00% |
| 2 | Octisalate | 5.00% | 5.00% | 5.00% |
| 3 | Homosalate | 7.50% | 7.50% | 7.50% |
| 4 | Benzophenone-3 | 0.49% | 0.49% | 0.49% |
| 5 | Octocrylene*** (OC) | 0.00% | 2.75% | 0.00% |
| 6 | C20 Methoxycrylene*** (C20MC) | 4.50% | 0.00% | 0.00% |
| 7 | Phenylethyl benzoate | 0.00% | 0.00% | 2.75% |
| 8 | Dimethicone (350 cSt) | 1.25% | 1.25% | 1.25% |
| 9 | Methyl trimethicone | 0.00% | 1.75% | 1.75% |
| 10 | VP/Eicosene copolymer | 1.00% | 1.00% | 1.00% |
| 11 | Cetearyl alcohol | 0.36% | 0.36% | 0.36% |
|  | Total Oil Ingredients | 23.10% | 23.10% | 23.10% |

TABLE 1-continued

COMPOSITIONS OF FORMULATIONS TESTED FOR PHOTOSTABILITY

| # | Ingredients | Example 1 (4.5% C20 Methoxycrylene) | Example 2 (POS: 2.75% OC Only) | Example 3 (NEG: No Photo-stabilizer) |
|---|---|---|---|---|
|  | Emulsifiers |  |  |  |
| 12 | Steareth-21 | 0.80% | 0.80% | 0.80% |
| 13 | Steareth-2 | 0.60% | 0.60% | 0.60% |
| 14 | Potassium cetyl phosphate & Hydrogenated palm glycerides | 3.00% | 3.00% | 3.00% |
|  | Total Emulsifiers | 4.40% | 4.40% | 4.40% |
| x | Water Phase Ingredients |  |  |  |
| 15 | Disodium EDTA | 0.10% | 0.10% | 0.10% |
| 16 | Glycerin | 4.00% | 4.00% | 4.00% |
| 17 | Benzyl alcohol | 1.00% | 1.00% | 1.00% |
| 18 | Methylparaben | 0.10% | 0.10% | 0.10% |
| 19 | Propylparaben | 0.05% | 0.05% | 0.05% |
| 20 | Water | 62.25% | 62.25% | 62.25% |
|  | Total Water Ingredients | 67.50% | 67.50% | 67.50% |
|  | Other Ingredients |  |  |  |
| 21 | Acrylamide/Sodium acryloyldimethyl taurate copolymer | 2.50% | 2.50% | 2.50% |
| 22 | Aluminum starch octenyl succinate | 2.50% | 2.50% | 2.50% |
|  | Total Other Ingredients | 5.00% | 5.00% | 5.00% |
|  | Total | 100.00% | 100.00% | 100.00% |

**Reported as Coefficients of Variation on report generated by Labsphere instrument
***On a molar basis, 4.5% C20 methoxycrylene is equal to 2.75% Octocrylene

PROCEDURE

1. Charge secondary vessel with 1-7. With stirring, heat to 90° C. Add in order 10-14. Continue stirring until homogeneous.
2. Charged primary vessel with water (20). With stirring, ad 15-16. Heat to 90° C.
3. Add oil phase (1-7, 10-14) to water phase (20, 15, 16). Stir vigorously for 10 minutes. Switch to homomixer and homogenize until temperature is below 55
4. When temperature of emulsion is below 55° C., switch to sweep stirring. Preblend 17-19. Add to emulsion when temperature is below 45° C.
5. Add 21 and continue sweep stirring as emulsion thickens. When smooth, add 22. Pre-blend 8 and 9 and add to batch.
6. Q.S. water and package when temperature of batch is less than 35° C.

The surprising photostability of the sunscreen composition of Example 1, Table I, including methoxycrylene, in comparison to the octocrylene of the prior art, is shown in FIG. 1, which is a graph of the data of Examples 1 through 3, above, and in the following SPF reports for Examples 4-6.

TABLE 2

| Results of Irradiation with 35 MED | Example 4 (7% Ethylhexyl methoxycrylene) | Example 5 (0% Ethylhexyl methoxycrylene) | Example 6 8.8% Octocrylene) |
|---|---|---|---|
| Loss of UVA protection** | −18.26% | −80.47% | −55.96% |
| Loss of UVB protection** | −6.46% | −52.01% | −4.51% |
| Loss of SPF** | −7.43% | −70.42% | −16.00% |

TABLE 2-continued

COMPOSITIONS OF FORMULATIONS TESTED FOR PHOTOSTABILITY

| # | Ingredients | CAB6-057 (7% Ethylhexyl methoxycrylene) | CAB6-058 (0% Ethylhexyl methoxycrylene) | CAB6-060 (0% Ethylhexyl methoxycrylene) |
|---|---|---|---|---|
| | Oil Phase Ingredients | | | |
| 1 | Avobenzone | 2.00% | 2.00% | 2.00% |
| 2 | Octyl methoxycinnamate (OMC) | 5.00% | 5.00% | 5.00% |
| 3 | Phenylethyl benzoate | 7.50% | 7.50% | 7.50% |
| 4 | Benzophenone-3 | 0.49% | 0.49% | 0.49% |
| 5 | Octocrylene | 1.80% | 1.80% | 8.80% |
| 6 | Ethylhexyl methoxycrylene*** | 7.00% | 0.00% | 0.00% |
| 7 | Polyisobutene | 0.00% | 7.00% | 0.00% |
| | Total Oil Ingredients | 23.79% | 23.79% | 23.79% |
| | Emulsifier | | | |
| 8 | Acrylates/C10-30 alkyl acrylate crosspolymer | 0.25% | 0.25% | 0.25% |
| 9 | Sorbitan laurate | 0.20% | 0.20% | 0.20% |
| | Total Emulsifiers | 0.45% | 0.45% | 0.45% |
| x | Water Phase Ingredients | | | |
| 10 | Disodium EDTA | 0.10% | 0.10% | 0.10% |
| 11 | Cetyl hydroxyethylcellulose | 0.30% | 0.30% | 0.30% |
| 12 | Glycerin | 4.00% | 4.00% | 4.00% |
| 13 | Benzyl alcohol | 1.00% | 1.00% | 1.00% |
| 14 | Methylparaben | 0.10% | 0.10% | 0.10% |
| 15 | Propylparaben | 0.05% | 0.05% | 0.05% |
| 16 | Triethanolamine | 0.40% | 0.40% | 0.40% |
| 17 | Water | 69.81% | 69.81% | 69.81% |
| | Total Water Ingredients | 75.76% | 75.76% | 75.76% |
| | Total | 100.00% | 100.00% | 100.00% |

**Reported as Coefficients of Variation on report generated by Labsphere instrument software.
PROCEDURE
1. Charge primary vessel with water (16). Dissolve 10. Heat to 85 degrees C. Disperse 11. Remove from heat. Continue stirring until 11 is fully dissolved.
2. In secondary vessel, add 2-7 and 9 with stirring. Add 1 and heat to 45 degrees C. Continue stirring until solution is clear.
3. Add 8 to oil and stir until completely incorporated.
4. When oil phase and water phase are 45 degrees C, add oil (1-7, 8, 9) to water (17, 10, 11). Maintain temperature and stir for 30 minutes.
5. Remove batch from heat. Preblend 12 and 16. Add to batch with stirring. Increase agitation as batch thickens.
6. Preblend 13-15, making sure that 14 and 15 are completely dissolved. Add to batch. Q.S. water and package when temperature of batch is less than 35° C.

Additional alkoxycrylene molecules were tested in accordance with the procedure indicated in Table 2, wherein radical $R_3$ of the alkoxycrylene of formula (I) has an $R_3$=ethyl hexyl (formula IV):

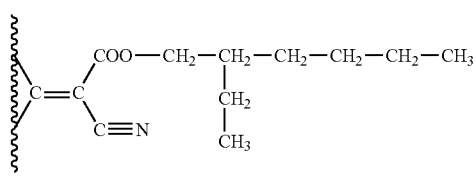

(IV)

Figure 2:
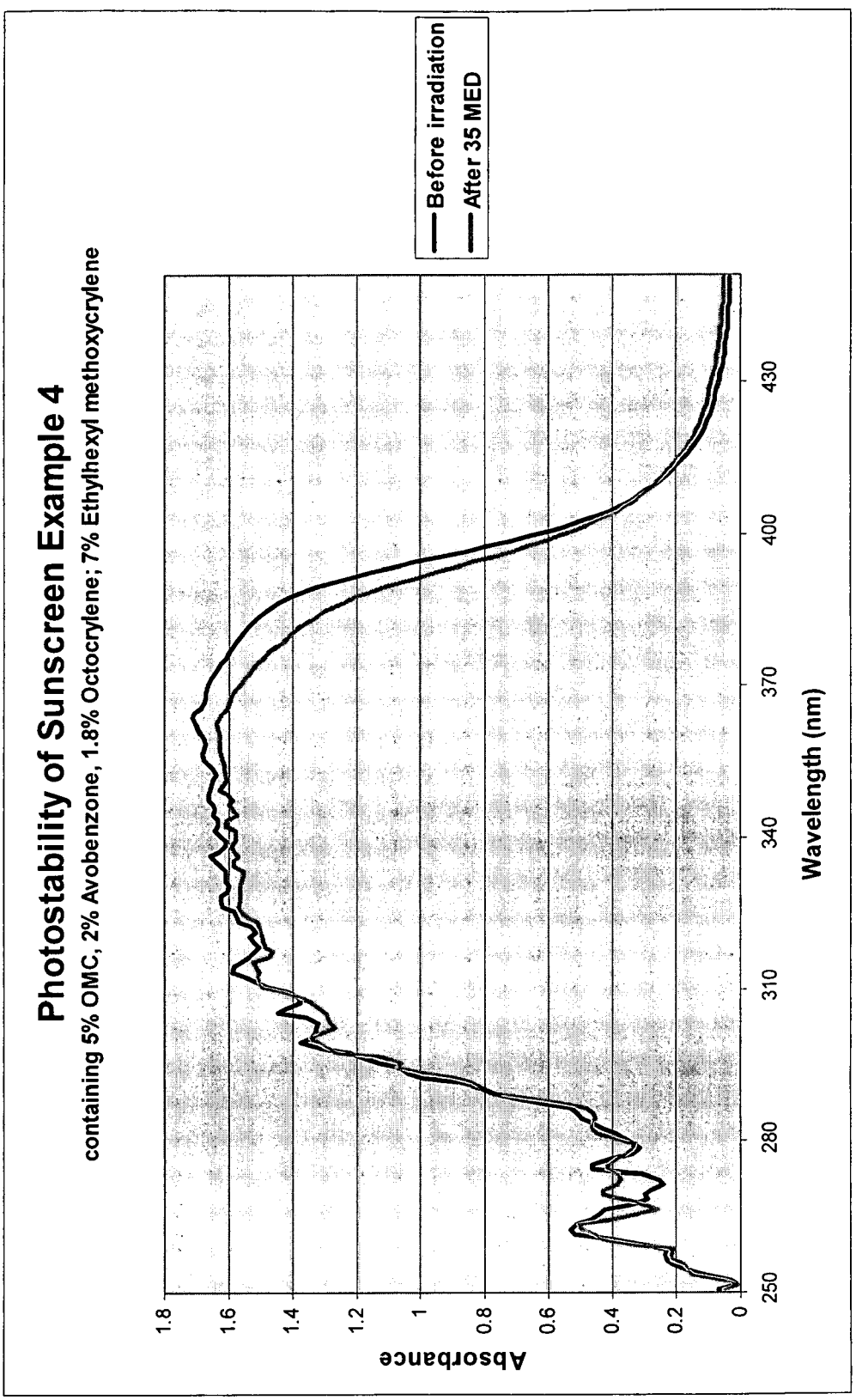
FIG. 2 is a graph showing the photostability of the sunscreen composition of Example 4 before and after irradiation with 35 MED of UV radiation.
Figure 3:
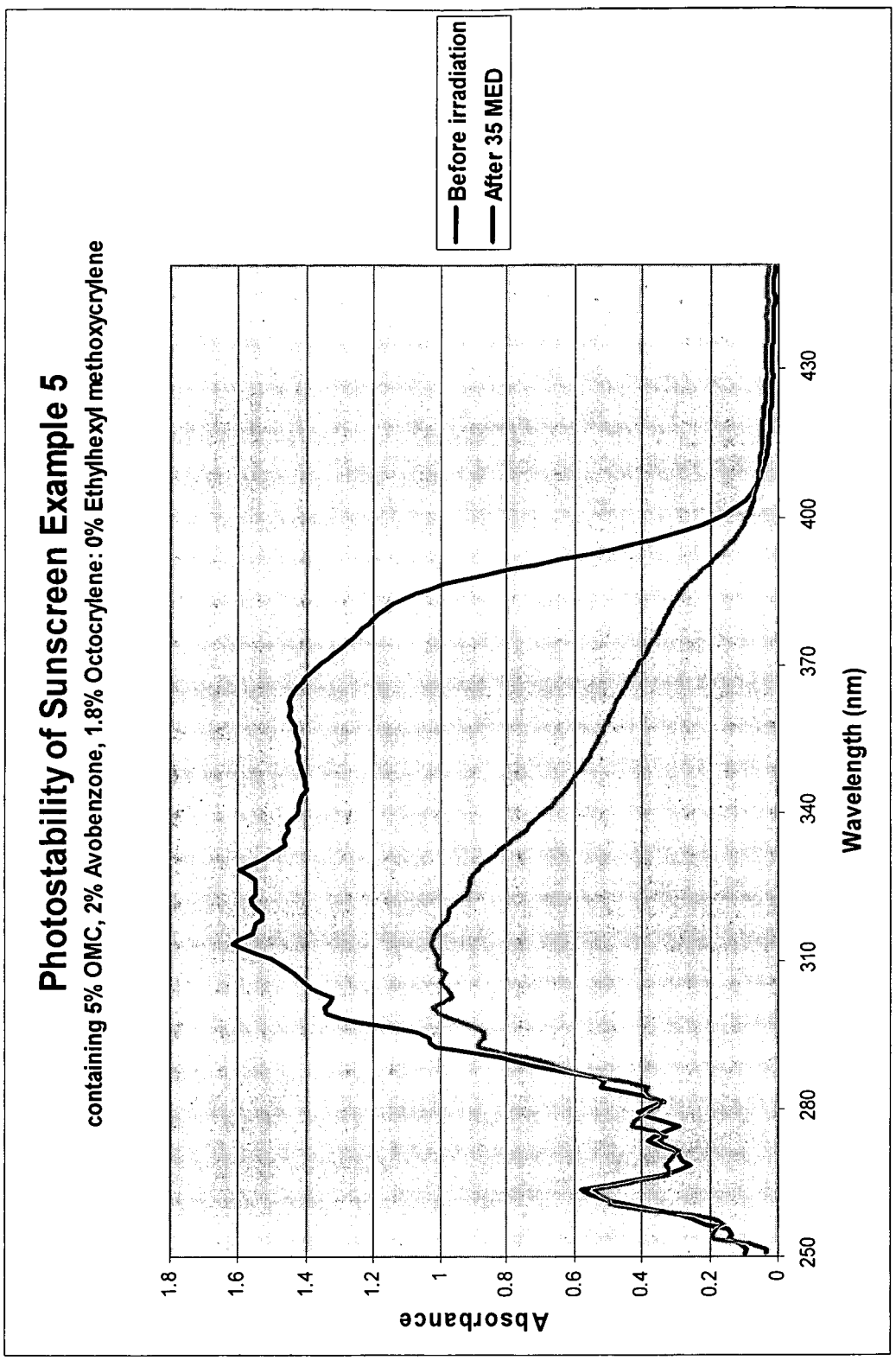
FIG. 3 is a graph showing the photostability of the sunscreen composition of Example 5 before and after irradiation with 35 MED of UV radiation.
Figure 4:
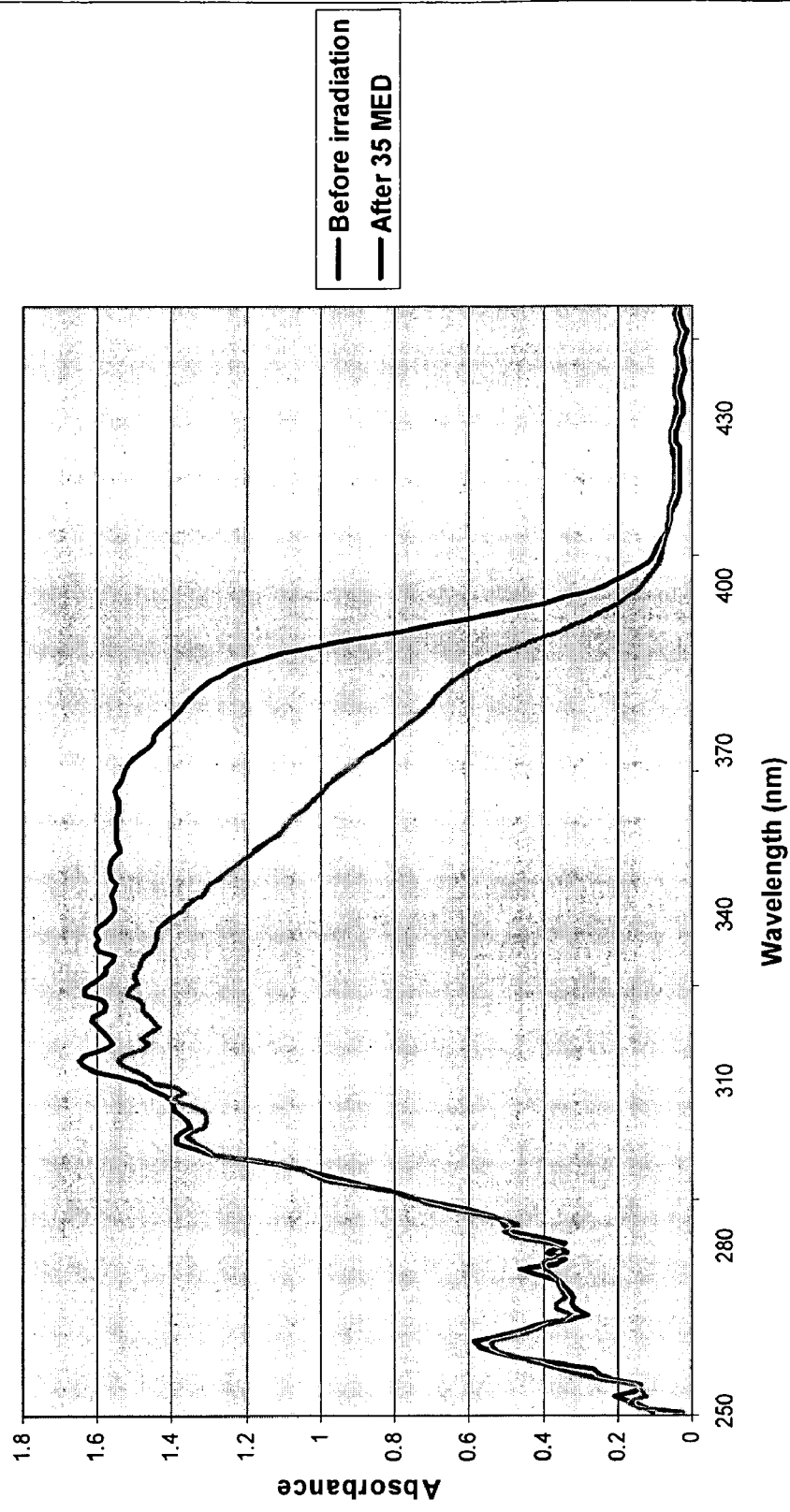
FIG. 4 is a graph showing the photostability of the sunscreen composition of Example 6 before and after irradiation with 35 MED of UV radiation.
Figure 5:
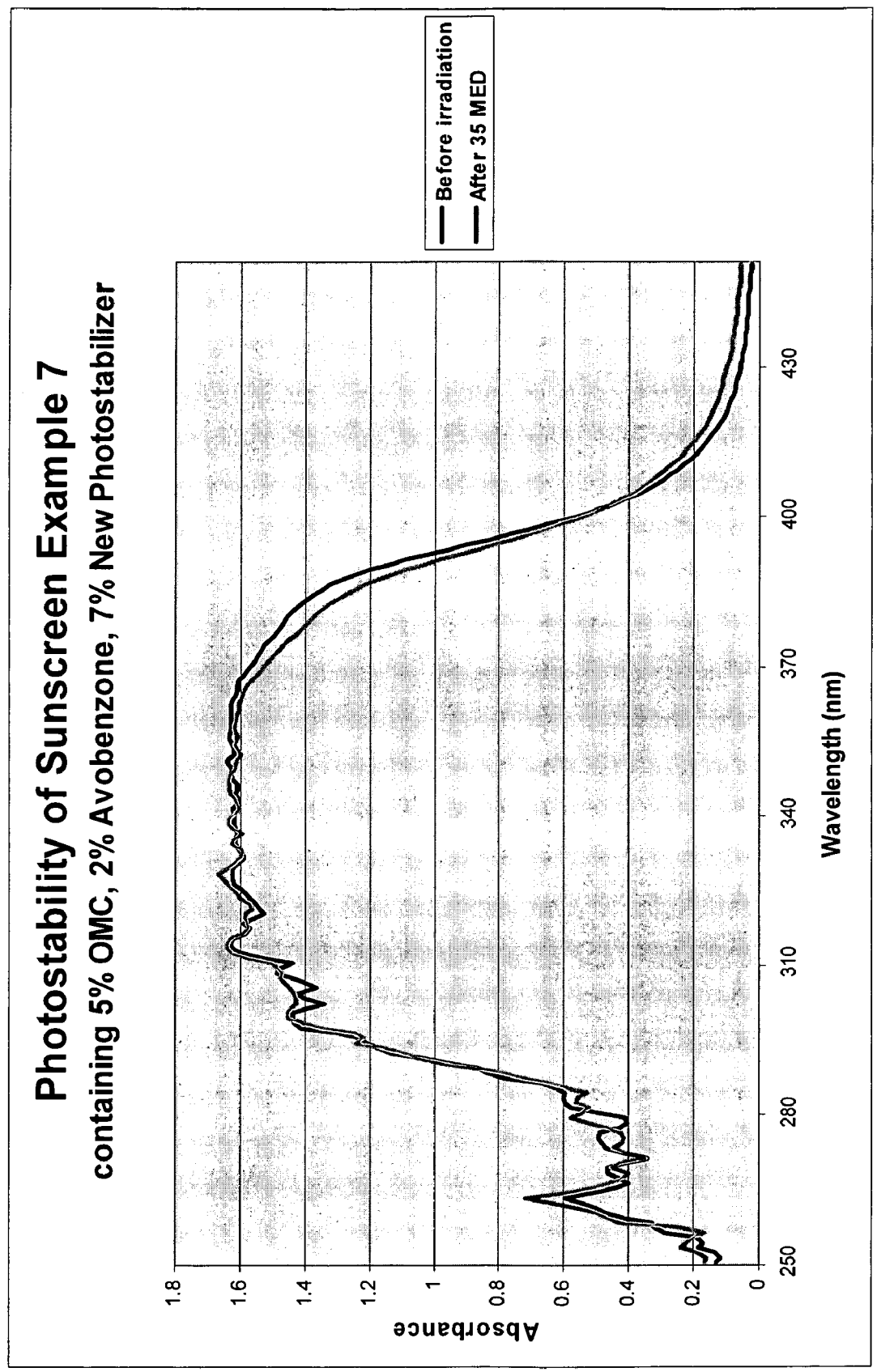
FIG. 5 is a graph showing the sunscreen composition of Example 7 before and after irradiation with 35 MED of UV radiation.

The data for the sunscreen composition of Example 4 is shown in the graph of FIG. 2 and the data for the composition of Example 5 is shown in the graph of FIG. 3. For Examples 4-6, the data of Example 6 (shown in graph form as FIG. 4) compares 7% ethylhexyl methoxycrylene (formula V) and 1.8% octocrylene (Example 4) to 8.8% octocrylene with no alkoxycrylene. As shown in the graph of FIG. 4 and the following SPF reports for Examples 4-6, the alkoxy crylenes described herein are unexpectedly better photostabilizers than octocrylene.

| SPF REPORT | | | |
|---|---|---|---|
| Sample: Example 4 UV Photostability | | | |
| Comment: 0, 35 MED | | | |
| Wavelength Range: 290-400 nm | | | |
| Units: | SPF | T(UVA) | T(UVB) |
| # of Scans: | 2 | 2 | 2 |
| Mean: | 24.67 | 4.52% | 5.43% |
| STD: | 1.83 | 0.83% | 0.35% |
| COV: | 7.43% | 18.26% | 6.46% |
| UVA/UVB Ratio: | 1.1 | | |
| Boots Star Rating: | N/A less than 5 Scans | | |
| Scan # | SPF | Critical Wavelength | |
| 1 | 25.97 | 385 | |
| 2 | 23.37 | 384 | |

-continued

SPF REPORT

Sample: Example 5 UV Photostability
Comment: 0, 35 MED
Wavelength Range: 290-400 nm

| Units: | SPF | T(UVA) | T(UVB) |
|---|---|---|---|
| # of Scans: | 2 | 2 | 2 |
| Mean: | 16.76 | 23.10% | 8.07% |
| STD: | 11.8 | 18.59% | 4.20% |
| COV: | 70.42% | 80.47% | 52.01% |
| UVA/UVB Ratio: | 0.72 | | |
| Boots Star Rating: | N/A less than 5 Scans | | |

| Scan # | SPF | Critical Wavelength |
|---|---|---|
| 1 | 25.11 | 380 |
| 2 | 8.41 | 372 |

Sample: Example 6 UV Photostability
Comment: 0, 35 MED
Wavelength Range: 290-400 nm

| Units: | SPF | T(UVA) | T(UVB) |
|---|---|---|---|
| # of Scans: | 2 | 2 | 2 |
| Mean: | 23.83 | 11.80% | 5.27% |
| STD: | 3.81 | 6.61% | 0.24% |
| COV: | 16.00% | 55.96% | 4.51% |
| UVA/UVB Ratio: | 0.88 | | |
| Boots Star Rating: | N/A less than 5 Scans | | |

-continued

SPF REPORT

| Scan # | SPF | Critical Wavelength |
|---|---|---|
| 1 | 26.52 | 382 |
| 2 | 21.13 | 375 |

As shown in the above-referenced formulations and data of Examples 4-6, the combination of avobenzone (UVA) with octylmethoxycinnamate (UVB) has particularly surprising results when combined with a stabilizing amount of an alkoxycrylene of formula I. It is well know that octocrylene stabilizes octyl methoxycinnamate (OMC), a UVB filter, but does not photostabilizer avobenzone, a UVA filter. In accordance with the compositions and methods described herein, it has been found that the alkoxycrylene of formula I photostabilize octyl methyoxycinnemate (OMC) much better than OMC, and also photostabilizes avobenzone. The alkoxycrylenes, therefore, can photostabilize sunscreen compositions. Accordingly, by adding an alkoxycrylene, both avobenzone and OMC can be photostabilized by the alkoxycrylene.

Example 4 (7% alkoxycrylene and 1.8% octocrylene) loses only 18.26% UVA; 6.46% UVB; and 7.43% of its SPM when subjected to 35 MED irradiation. The same formulation containing no alkoxycrylene (Example 5) loses 80.47% UVA; 52.01% UVB; and 70.42% of its SPF. Example 6, containing 8.8% octocrylene and no alkoxycrylene loses 55.96% UVA; 4.51% UVB (octocrylene photostabilizes OMC but not avobenzone); and 16% of its SPF, Examples 4, 5 and 6 are shown graphically in FIGS. 2, 3 and 4.

Additional sunscreen compositions were prepared containing 0 wt. %, 3 wt. % and 5 wt. % 2-ethylhexyl methoxycrylene, as shown in Examples 7-10 in Table 3:

TABLE 3

| # | Ingredients | Example 7 (5% 2-EH Methoxycrylene) | Example 8 (3% 2-EH methoxycrylene) | Example 9 (0% 2-EH methoxycrylene) | Example 10 (3% 2-EH methoxycrylene) |
|---|---|---|---|---|---|
| | Oil Phase Ingredients | | | | |
| 1 | Avobenzone | 3.00% | 3.00% | 3.00% | 3.00% |
| 2 | Octisalate | 5.00% | 5.00% | 5.00% | 5.00% |
| 3 | Octinoxate (Octyl methoxycinnamate or OMC or MCX) | 7.50% | 7.50% | 7.50% | 7.50% |
| 4 | Benzophenone-3 | 0.49% | 0.49% | 0.49% | 0.49% |
| 5 | Octocrylene*** (OC) | 5.00% | 7.00% | 10.00% | 10.00% |
| 6 | Ethylhexyl methoxycrylene*** (2-EH methoxycrylene or MOC) | 5.00% | 3.00% | 0.00% | 3.00% |
| 7 | Cetearyl alcohol | 0.35% | 0.35% | 0.35% | 0.35% |
| 8 | C30-38 Olefin/Isopropyl maleate/MA copolymer | 0.80% | 0.80% | 0.80% | 0.80% |
| | Total Oil Ingredients | 27.14% | 27.14% | 27.14% | 30.14% |
| | Emulsifiers | | | | |
| 9 | Steareth-21 | 0.45% | 0.45% | 0.00% | 0.00% |
| 10 | Steareth-2 | 0.65% | 0.65% | 0.00% | 0.00% |
| 11 | Glyceryl stearate/PEG-100 stearate | 0.00% | 0.00% | 1.00% | 1.00% |
| 12 | Potassium cetyl phosphate & Hydrogenated palm glycerides | 3.00% | 3.00% | 3.00% | 3.00% |
| | Total Emulsifiers | 4.10% | 4.10% | 4.00% | 4.00% |
| x | Water Phase Ingredients | | | | |
| 13 | Disodium EDTA | 0.10% | 0.10% | 0.10% | 0.10% |
| 14 | Tromethamine | 0.04% | 0.04% | 0.04% | 0.04% |
| 15 | Glycerin | 4.00% | 4.00% | 4.00% | 4.00% |
| 16 | Benzyl alcohol | 1.00% | 1.00% | 1.00% | 1.00% |
| 17 | Methylparaben | 0.10% | 0.10% | 0.10% | 0.10% |

TABLE 3-continued

| # | Ingredients | Example 7 (5% 2-EH Methoxycrylene) | Example 8 (3% 2-EH methoxycrylene) | Example 9 (0% 2-EH methoxycrylene) | Example 10 (3% 2-EH methoxycrylene) |
|---|---|---|---|---|---|
| 18 | Propylparaben | 0.05% | 0.05% | 0.05% | 0.05% |
| 19 | Water | 58.47% | 58.47% | 58.57% | 55.57% |
|   | Total Water Ingredients | 63.76% | 63.76% | 63.86% | 60.86% |
|   | Other Ingredients | | | | |
| 20 | Acrylamide/Sodium acryloyldimethyltaurate copolymer (and) Isohexadecane (and) Polysorbate 80 | 2.00% | 2.00% | 2.00% | 2.00% |
| 21 | Aluminum starch octenyl succinate | 3.00% | 3.00% | 3.00% | 3.00% |
|   | Total Other Ingredients | 5.00% | 5.00% | 5.00% | 5.00% |
|   | Total | 100.00% | 100.00% | 100.00% | 100.00% |

PROCEDURE
1. Charge secondary vessel with 1-9. With stirring, heat to 90° C. Add in order 9-12. Continue stirring until homogeneous.
2. Charged primary vessel with water (19). With stirring, add 14-15. Heat to 90° C.
3. Add oil phase (1-8, 9-12) to water phase (19, 14, 15). Stir vigorously for 10 minutes. Switch to homomixer and homogenize until temperature is below 60° C.
4. When temperature of emulsion is below 60° C., switch to sweep stirring. Preblend 15-18. Add to emulsion when temperature is below 45° C.
5. Add 20 and continue sweep stirring as emulsion thickens. When smooth, add 21.
6. Q.S. water and package when temperature of batch is less than 35° C.
Q.S. = quantity sufficient The results were as follows and clearly show that adding more alkoxycrylene to sunscreen formulation provides more Photostabilization of both UVA and UVB filters. Example 7, having the most MOC (5%) and the least OC (5%) provided the best results.

| Results of Irradiation with 20 MED | Example 7 5% OC/5% MOC | Example 8 7% OC/3% MOC | Example 9 10% OC/0% MOC | Example 10 10% OC/3% MOC |
|---|---|---|---|---|
| UVA1/UV ratio before UV irradiation | 0.84 | 0.83 | 0.79 | 0.83 |
| UVA1/UV ratio after 20 MED | 0.76 | 0.71 | 0.54 | 0.70 |
| Difference after irradiation | 0.09 | 0.12 | 0.25 | 0.13 |
| % change | 10.00% | 15.00% | 32.00% | 16.00% |

OC = Octocrylene;
MOC = Ethylhexyl Methoxycrylene;
UVA1 = total area under curve from 340 to 400 nm;
UV = total area under curve from 290 to 400 nm More sunscreen compositions were prepared containing 0, 2, 4 and 6 wt. % 2-ethylhexyl methoxycrylene to test the photostabilizing capacity of the methoxycrylenes to photostabilize avobenzone and other photodegradable UV-absorbers, as shown in Examples 11-14 in Table 4:

TABLE 4

| # | Ingredients | Example 11 0% MOC | Example 12 2% MOC | Example 13 4% MOC | Example 14 6% MOC |
|---|---|---|---|---|---|
|   | Oil Phase Ingredients | | | | |
| 1 | Avobenzone | 3.00% | 3.00% | 3.00% | 3.00% |
| 2 | Octisalate | 5.00% | 5.00% | 5.00% | 5.00% |
| 3 | Homosalate | 7.50% | 7.50% | 7.50% | 7.50% |
| 4 | Butyloctyl benzoate | 9.00% | 7.00% | 5.00% | 3.00% |
| 5 | Ethylhexyl methoxycrylene*** (2-EH methoxycrylene or MOC) | 0.00% | 2.00% | 4.00% | 6.00% |
| 6 | Cetearyl alcohol | 0.35% | 0.35% | 0.35% | 0.35% |
| 7 | VP/Eicosene copolymer | 1.00% | 1.00% | 1.00% | 1.00% |
|   | Total Oil Ingredients | 25.85% | 25.85% | 25.85% | 25.85% |

TABLE 4-continued

| # | Ingredients | Example 11 0% MOC | Example 12 2% MOC | Example 13 4% MOC | Example 14 6% MOC |
|---|---|---|---|---|---|
| | Emulsifiers | | | | |
| 8 | Steareth-21 | 0.00% | 0.00% | 0.00% | 0.00% |
| 9 | Steareth-2 | 0.00% | 0.00% | 0.00% | 0.00% |
| 10 | Glyceryl stearate/PEG-100 stearate | 1.00% | 1.00% | 1.00% | 1.00% |
| 11 | Potassium cetyl phosphate & Hydrogenated palm glycerides | 3.00% | 3.00% | 3.00% | 3.00% |
| | Total Emulsifiers | 4.00% | 4.00% | 4.00% | 4.00% |
| x | Water Phase Ingredients | | | | |
| 12 | Disodium EDTA | 0.10% | 0.10% | 0.10% | 0.10% |
| 13 | Glycerin | 4.00% | 4.00% | 4.00% | 4.00% |
| 14 | Benzyl alcohol | 1.00% | 1.00% | 1.00% | 1.00% |
| 15 | Methylparaben | 0.10% | 0.10% | 0.10% | 0.10% |
| 16 | Propylparaben | 0.05% | 0.05% | 0.05% | 0.05% |
| 17 | Water | 59.90% | 59.90% | 59.90% | 59.90% |
| | Total Water Ingredients | 65.15% | 65.15% | 65.15% | 65.15% |
| | Other Ingredients | | | | |
| 18 | Acrylamide/Sodium acryloyldimethyltaurate copolymer (and) Isohexadecane (and) Polysorbate 80 | 2.00% | 2.00% | 2.00% | 2.00% |
| 19 | Aluminum starch octenyl succinate | 3.00% | 3.00% | 3.00% | 3.00% |
| | Total Other Ingredients | 5.00% | 5.00% | 5.00% | 5.00% |
| | Total | 100.00% | 100.00% | 100.00% | 100.00% |

PROCEDURE
1. Charge secondary vessel with 1-7. With stirring, heat to 90° C. Add in order 10-11. Continue stirring until homogeneous.
2. Charged primary vessel with water (17). With stirring, add 12. Heat to 90° C.
3. Add oil phase (1-7, 10-11) to water phase (17, 12). Stir vigorously for 10 minutes. Switch to homomixer and homogenize until temperature is below 60° C.
4. When temperature of emulsion is below 60° C., switch to sweep stirring. Preblend 13-16. Add to emulsion when temperature is below 45° C.
5. Add 18 and continue sweep stirring as emulsion thickens. When smooth, add 19.
6. Q.S. water and package when temperature of batch is less than 35° C.
Q.S. = quantity sufficient The results were as follows:

| | Example 11 | Example 12 | Example 13 | Example 14 |
|---|---|---|---|---|
| Results of Irradiation with 20 MED | 0% MOC | 2% MOC | 4% MOC | 6% MOC |
| UVA1/UV ratio before UV irradiation | 0.88 | 0.91 | 0.90 | 0.91 |
| UVA1/UV ratio after 20 MED | 0.32 | 0.85 | 0.88 | 0.90 |
| Difference after irradiation | 0.56 | 0.06 | 0.02 | 0.01 |
| % change | 63.67% | 6.43% | 2.00% | 1.04% |

MOC = Ethylhexyl Methoxycrylene;
UVA1 = total area under curve from 340 to 400 nm;
UV = total area under curve from 290 to 400 nm It should be noted that the sunscreen formulations of Examples 11-14 contain no octyl methoxycinnemate or other photostabilizers. It is clear from the data of Examples 11-14 that the alkoxycrylene of formula I photostabilize avobenzone and other dibenzoylmethane derivatives with surprising efficacy.

Additional sunscreen compositions were prepared containing 5 wt. % 2-ethylhexyl methoxycrylene with and without 1.5 wt. % Tinosorb S or Tinosorb M, as shown in Examples 15 and 16 in Table 5:

TABLE 5

| # | Ingredients | Example 15 1.5% Bemotrizinol/5% MOC | Example 16 5% Bisoctrizole/5% MOC |
|---|---|---|---|
| | Oil Phase Ingredients | | |
| 1 | Avobenzone | 3.00% | 3.00% |
| 2 | Octisalate | 5.00% | 5.00% |

TABLE 5-continued

| # | Ingredients | Example 15 1.5% Bemotrizinol/5% MOC | Example 16 5% Bisoctrizole/5% MOC |
|---|---|---|---|
| 3 | Octinoxate (Octyl methoxycinnamate or OMC or MCX) | 7.50% | 7.50% |
| 4 | Bemotrizinol (Tinosorb S) | 1.50% | 0.00% |
| 6 | Ethylhexyl methoxycrylene*** (2-EH methoxycrylene or MOC) | 5.00% | 5.00% |
| 7 | Trideceth-12 | 1.00% | 1.00% |
| 8 | VP/Eicosene copolymer | 1.00% | 1.00% |
| 9 | Behenyl alcohol + Glyceryl stearate + Glyceryl stearate citrate + Sodium dicocoylethylenediamine PEG-15 sulfate | 1.00% | 1.00% |
| | Total Oil Ingredients | 25.00% | 23.50% |
| | Emulsifiers | | |
| | (See 7, 9, 12) | 0.00% | 0.00% |
| | Total Emulsifiers | 0.00% | 0.00% |
| x | Water Phase Ingredients | | |
| 10 | Disodium EDTA | 0.10% | 0.10% |
| 11 | Xanthan gum | 0.10% | 0.10% |
| 12 | Sodium dicocoylethylenediamine PEG-15 sulfate + Sodium lauroyl lactylate | 1.00% | 1.00% |
| 13 | Glycerin | 4.00% | 4.00% |
| 14 | Benzyl alcohol | 1.00% | 1.00% |
| 15 | Methylparaben | 0.10% | 0.10% |
| 16 | Propylparaben | 0.05% | 0.05% |
| 17 | Water | 63.65% | 60.15% |
| | Total Water Ingredients | 70.00% | 66.50% |
| | Other Ingredients | | |
| 18 | Bisoctrizole (Tinosorb M) | 0.00% | 5.00% |
| 19 | Acrylamide/Sodium acryloyldimethyltaurate copolymer (and) Isohexadecane (and) Polysorbate 80 | 2.00% | 2.00% |
| 20 | Aluminum starch octenyl succinate | 3.00% | 3.00% |
| | Total Other Ingredients | 5.00% | 10.00% |
| | Total | 100.00% | 100.00% |

PROCEDURE
1. Charge secondary vessel with 1-9. With stirring, heat to 70° C. Continue stirring until homogeneous. Maintain temperature.
2. Charged a third vessel with water (19). Dissolve 10 with stirring. Add 11 and stir until Xanthan gum is completely dissolved.
3. Place ⅓ of (2) in primary vessel. Heat to 65° C. Add 12 and stir until homogeneous.
4. Add oil phase (1-9) to water (10-12) in primary vessel. Homogenize for two minutes, or until emulsion is fully formed.
5. Remove batch from heat. Slowly add balance of water (see Step 2) to emulsion with stirring. Stir while cooling.
6. Preblend 13-16. Add to batch with stirring. Add 18 to batch with stirring.
7. Add 19 and stir until smooth and homogeneous. Add 20 and stir until fully incorporated. Q.S. water. Package when batch is < 35° C.
Q.S. = quantity sufficient The results were as follows:

| Results of Irradiation with 20 MED | Example 15 1.5% Bemotrizinol/ 5% MOC | Example 16 5% Bisoctrizole/ 5% MOC |
|---|---|---|
| UVA1/UV ratio before UV irradiation | 0.87 | 0.87 |
| UVA1/UV ratio after 20 MED | 0.81 | 0.84 |
| Difference after irradiation | 0.06 | 0.03 |
| % change | 6.66% | 3.55% |

MOC = Ethylhexyl Methoxycrylene;
UVA1 = total area under curve from 340 to 400 nm;
UV = total area under curve from 290 to 400 nm Tinsorb S of Examples 15 and 16 is a known UVA and UVB photostabilizer (more effective in the UVA range) for photostabilizing both avobenzone and octyl methoxycinnamate. Surprisingly, as shown in the data of Examples 15 and 16 (both Examples include 5% MOC) omitting the Tinsorb S from Example 16 makes very little difference in photostabilizing the combination of avobenzone and OMC.

Additional sunscreen formulations were tested containing 5 wt. % butyloctyl methoxycrylene and a triazine derivative (Uvinul T-150); a benzophenone derivative (Uvinul A Plus); and three water soluble UV filters (Mexonylsx; Neo Heliopan AP; and Neo Heliopan Hydro), as shown in examples 17-21 of table 6:

TABLE 6

| Ingredients | Example 17 2% Uvinul T-150 | Example 18 2% Uvinul A Plus | Example 19 2% Mexoryl SX | Example 20 2% Neo Hellopan AP | Example 21 2% Neo Hellopan Hydro |
|---|---|---|---|---|---|
| Oil Phase Ingredients | | | | | |
| 1 Avobenzone | 3.00% | 3.00% | 3.00% | 3.00% | 3.00% |
| 2 Octisalate | 5.00% | 5.00% | 5.00% | 5.00% | 5.00% |
| 3 Octinoxate (Octyl methoxycinnamate or OMC or MCX) | 7.50% | 7.50% | 7.50% | 7.50% | 7.50% |
| 4 Octyl triazone (Uvinul T-150, BASF) | 2.00% | 0.00% | 0.00% | 0.00% | 0.00% |
| 5 Diethylamino Hydroxybenzoyl Hexyl Benzoate (Uvinul A Plus, BASF) | 0.00% | 2.00% | 0.00% | 0.00% | 0.00% |
| 6 Butyloctyl methoxycrylene | 5.00% | 5.00% | 5.00% | 5.00% | 5.00% |
| 7 VP/Eicosene copolymer | 1.00% | 1.00% | 1.00% | 1.00% | 1.00% |
| Total Oil Ingredients | 23.50% | 23.50% | 21.50% | 21.50% | 21.50% |
| Emulsifiers | | | | | |
| 8 Stearyl alcohol | 1.00% | 1.00% | 1.00% | 1.00% | 1.00% |
| 9 Glyceryl stearate | 1.00% | 1.00% | 1.00% | 1.00% | 1.00% |
| 10 Polyglyceryl-3 methyl glucose distearate | 3.00% | 3.00% | 3.00% | 3.00% | 3.00% |
| Total Emulsifiers | 5.00% | 5.00% | 5.00% | 5.00% | 5.00% |
| Water Phase Ingredients | | | | | |
| 11 Disodium EDTA | 0.10% | 0.10% | 0.10% | 0.10% | 0.10% |
| 12 Ecamsule neutralized with triethanolamine (Mexoryl SX, Chemex) | 0.00% | 0.00% | 2.00% | 0.00% | 0.00% |
| 13 Bisdisulizole disodium (Neo Heliopan AP, Symrise) | 0.00% | 0.00% | 0.00% | 2.00% | 0.00% |
| 14 Ensulizole neutralized with triethanolamine (Neo Heliopan Hydro, Symrise) | 0.00% | 0.00% | 0.00% | 0.00% | 2.00% |
| 15 Glycerin | 4.00% | 4.00% | 4.00% | 4.00% | 4.00% |
| 16 Benzyl alcohol | 1.00% | 1.00% | 1.00% | 1.00% | 1.00% |
| 17 Methylparaben | 0.10% | 0.10% | 0.10% | 0.10% | 0.10% |
| 18 Propylparaben | 0.05% | 0.05% | 0.05% | 0.05% | 0.05% |
| 19 Water | 61.25% | 61.25% | 61.25% | 61.25% | 61.25% |
| Total Water Ingredients | 66.50% | 66.50% | 68.50% | 68.50% | 68.50% |
| Other Ingredients | | | | | |
| 20 Acrylamide/Sodium acryloyldimethyltaurate copolymer (and) Isohexadecane (and) Polysorbate 80 | 2.00% | 2.00% | 2.00% | 2.00% | 2.00% |
| 21 Aluminum starch octenyl succinate | 3.00% | 3.00% | 3.00% | 3.00% | 3.00% |
| Total Other Ingredients | 5.00% | 5.00% | 5.00% | 5.00% | 5.00% |
| Total | 100.00% | 100.00% | 100.00% | 100.00% | 100.00% |

PROCEDURE
1. Charge secondary vessel with 1-7.. With stirring, heat to 80° C. Add 8-10. Continue stirring until homogeneous.
2. In another secondary vessel, dissolve 12 or 13 or 14 in water and set aside.
3. Charged primary vessel with water (19), except amount necessary for Step 2.. Dissolve 11. Heat to 80° C.
4. Add oil (1-10) to water (11, 19) with stirring. Remove from heat. Homogenize for 10 minutes. Stir while cooling.
5. When temperature is below 45° C., add pre-mixed 15-18.
6. Add pre-dissolved 12, 13, or 14.
7. Add 20 and continue sweep stirring as emulsion thickens. When smooth, add 21.
8. Q.S. water and package when temperature of batch is less than 35° C.
Q.S. = quantity sufficient Two more sunscreen formulations (Examples 22 and 23) were prepared each containing butyloctyl methoxycrylene, and Example 23 also containing Tinasorb® S and Tinasorb® M. As shown in the results, the combination of an alkoxycrylene, together with a dibenzoylmethane derivative, a cinnamate ester, Tinasorb® S and Tinasorb® M, avobenzone and octyl methoxycinnamate is particularly photostable:

| | Example 22 0% TinS/0% TinM/7% BMOC | Example 23 2% TinS/5% TinM/5% BMOC |
|---|---|---|
| Results of Irradiation with 20 MED | Sheet 1 | |
| UVA1/UV ratio before UV irradiation | 0.84 | 0.85 |
| UVA1/UV ratio after 20 MED | 0.78 | 0.83 |
| Difference after irradiation | 0.06 | 0.02 |
| % change | 7.14% | 2.35% |

| Ingredients | Example 22 0% TinS/0% TinM/7% BMOC | Example 23 2% TinS/5% TinM/5% BMOC |
|---|---|---|
| Oil Phase Ingredients | | |
| 1 Avobenzone | 3.00% | 3.00% |
| 2 Octisalate | 5.00% | 5.00% |
| 3 Octinoxate (Octyl methoxycinnamate or OMC or MCX) | 7.50% | 7.50% |
| 4 Bemotrizinol (Tinosorb S) | 0.00% | 2.00% |
| 5 Butyloctyl methoxycrylene*** (C12 methoxycrylene or BMOC) | 7.00% | 5.00% |
| 7 Trixlecetin-12 | 1.00% | 1.00% |
| 8 VP/Eicosene copolymer | 1.00% | 1.00% |
| 9 Behenyl alcohol + Glyceryl stearate + Glyceryl stearate citrate + Sodium dicocoylethylenediamine PEG-15 sulfate | 1.00% | 1.00% |
| Total Oil Ingredients | 25.50% | 25.50% |
| Emulsifiers | | |
| (See 7.9.12) | 0.00% | 0.00% |
| Total Emulsifiers | 0.00% | 0.00% |
| Water Phase Ingredients | | |
| 10 Disodium EDTA | 0.10% | 0.10% |
| 11 Xanthan gum | 0.10% | 0.10% |
| 12 Sodium dicocoylethylenediamine PEG-15 sulfate + Sodium leuaryl acrylate | 1.00% | 1.00% |
| 13 Glycerin | 4.00% | 4.00% |
| 14 Benzyl alcohol | 1.00% | 1.00% |
| 15 Methylparaben | 0.10% | 0.10% |
| 16 Propylparaben | 0.05% | 0.05% |
| 17 Water | 63.15% | 58.15% |
| Total Water Ingredients | 69.50% | 64.50% |
| Other Ingredients | | |
| 18 Bisoctizole (Tinsorb M) | 0.00% | 5.00% |
| 19 Acrylamide Sodium acryloyldimethyltaurate copolymer (and) Isohexadecane (and) Polysorbate 80 | 2.00% | 2.00% |
| 20 Aluminum starch octenyl succinate | 3.00% | 3.00% |
| Total Other Ingredients | 5.00% | 10.00% |
| Total | 100.00% | 100.00% |

BMOC = Butyloctyl methoxycrylene;
TinS = Tinosorb S (Bemotrizinol); TinM = Tinosorb M (Bisoctrizole)
UVA1 = total area under curve from 340 to 400 nm;
UV = total area under curve from 290 to 400 nm
PROCEDURE
1. Charge secondary vessel with 1-9. With stirring, heat to 70° C.. Continue stirring until homogeneous. Maintain temperature.
2. Charged a third vessel with water (19). Dissolve 10 with stirring. Add 11 and stir until Xanthan gum is completely dissolved.
3. Place ⅓ of (2) in primary vessel. Heat to 85° C.. Add 12 and stir until homogeneous.
4. Add oil phase (1-9) to water (10-12) in primary vessel. Homogenize for two minutes or until emulsion is fully formed.
5. Remove batch from heat. Slowly add balance of water (see Step 2) to emulsion with stirring. Stir while cooling.
6. Preblend 13-16. Add to batch with stirring. Add 18 to batch with stirring.
7. Add 19 and stir until smooth and homogenous. Add 20 and stir until fully incorporated. Q.S. water. Package when batch is <35° C..
Q.S. = quantity sufficient In addition to the simple ester alkoxy crylene compounds of formula (I)-(V), the alkoxy crylene moieties can be attached as one or more terminal moieties on a polyester molecule, such as the alkoxy derivatives of the Di (NPG Crylene) Fumerate polyesters disclosed in this assignee's U.S. Pat. No. 7,235,587 ('587), hereby incorporated by references, as shown in formula (VI):

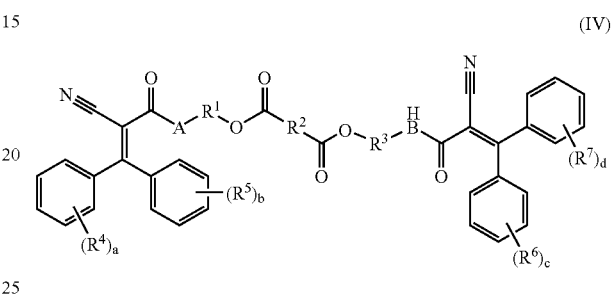

(IV)

wherein A and B are the same or different and are selected from the group consisting of oxygen, amino and sulfur; $R^1$ and $R^3$ are the same or different and are selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkylene, $C_2$-$C_{30}$ substituted alkyne, aryl, substituted aryl, heteroaryl, heterocycloalkyl, substituted heteroaryl and substituted heterocycloalkyl; $R^2$ is selected from the group consisting of $C_1$-$C_{30}$ alkyl, $C_2$-$C_{30}$ alkylene, $C_2$-$C_{30}$ alkyne, $C_3$-$C_8$ cycloalkyl, $C_1$-$C_{30}$ substituted alkyl, $C_3$-$C_8$ substituted cycloalkyl, $C_1$-$C_{30}$ substituted alkylene, $C_2$-$C_{30}$ substituted alkyne; $R^4$, $R^5$, $R^6$ and $R^7$ are the same or different and are selected from the group consisting of $C_1$-$C_{30}$ alkoxy straight chain on branched, and a, b, c and d are each either 0 or 1, and a, b, c and d add up to 1, 2, 3, or 4.

The invention claimed is:

1. A method of increasing the UV absorbing life of a sunscreen composition containing (a) a dibenzoylmethane derivative that reaches a singlet excited state or fluoresces when exposed to UV radiation and (b) a cinnamate ester comprising adding a compound of formula (I) in an amount effective to quench the singlet excited state energy from the dibenzoylmethane derivative and transfer the singlet excited state energy from the dibenzoylmethane derivative to the compound of formula (I) thereby returning the dibenzoylmethane derivative to its ground state so that the dibenzoylmethane derivative can absorb more photons from ultraviolet light before it undergoes a photochemical reaction destructive to its UV-absorbing capability thereby photostabilizing (a) and (b)

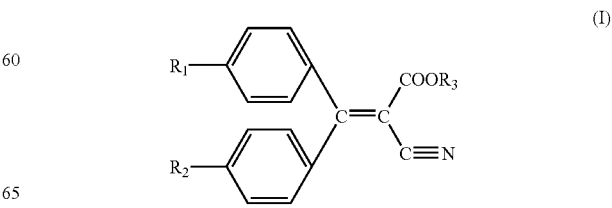

(I)

wherein one of $R_1$ and $R_2$ is a straight or branched chain $C_1$-$C_{30}$ alkoxy radical, and the non-alkoxy $R_1$ or $R_2$ is hydrogen; and $R_3$ is a straight or branched chain $C_1$-$C_{30}$ alkyl radical.

2. The method of claim 1, wherein the cinnamate ester is an ester of an alkoxycinnamate.

3. The method of claim 2, wherein the alkoxycinnamate ester is a methoxycinnamate ester.

4. The method of claim 3, wherein the cinnamate ester is selected from the group consisting of 2-ethyihexyl p-methoxycinnamate, isoamyl p-methoxycinnamate, and a combination thereof.

5. The method of claim 4, wherein the cinnamate ester is 2-ethylhexyl p-methoxycinnamate.

6. The method of claim 5, wherein the dibenzoylmethane derivative comprises butylmethoxy dibenzoylmethane.

7. The method of claim 1, wherein $R_1$ or $R_2$ of formula (I) is a methoxy radical.

8. The method of claim 7, wherein the compound of formula (I) is added in an amount sufficient to absorb the singlet excited state energy of both the dibenzoylmethane derivative and the cinnamate ester when both are subjected to UV radiation.

9. The method of claim 1, wherein the compound of formula (I) is present in an amount in the weight range of 0.1% to 20%, based on the total weight of the composition.

10. The method of claim 9, wherein the compound of formula (I) is present in an amount in the weight range of 0.1% to 10%, based on the total weight of the composition.

11. The method of claim 10, wherein the compound of formula (I) is present in an amount in the weight range of 3% to 8%, based on the total weight of the composition.

12. The method of claim 10, wherein the compound of formula (I) is present in an amount in the weight range of 0.1% to 5%, based on the total weight of the composition.

* * * * *

UNITED STATES PATENT AND TRADEMARK OFFICE
CERTIFICATE OF CORRECTION

PATENT NO. : 7,588,702 B2  Page 1 of 1
APPLICATION NO. : 12/022758
DATED : September 15, 2009
INVENTOR(S) : Craig A. Bonda et al.

It is certified that error appears in the above-identified patent and that said Letters Patent is hereby corrected as shown below:

In the Claims:

At Column 47, line 10, "2-ethyihexyl" should be -- 2-ethylhexyl --.

Signed and Sealed this

Fourth Day of May, 2010

David J. Kappos
*Director of the United States Patent and Trademark Office*